United States Patent
LeMoyne et al.

(10) Patent No.: US 12,415,076 B1
(45) Date of Patent: Sep. 16, 2025

(54) MULTIDISCIPLINARY DESIGN OPTIMIZATION OF NEUROMODULATION SYSTEMS

(71) Applicants: Robert LeMoyne, Running Springs, CA (US); Timothy Mastroianni, Pittsburgh, PA (US)

(72) Inventors: Robert LeMoyne, Running Springs, CA (US); Timothy Mastroianni, Pittsburgh, PA (US)

( * ) Notice: Subject to any disclaimer, the term of this patent is extended or adjusted under 35 U.S.C. 154(b) by 481 days.

(21) Appl. No.: 17/863,245

(22) Filed: Jul. 12, 2022

Related U.S. Application Data

(60) Provisional application No. 63/221,438, filed on Jul. 13, 2021.

(51) Int. Cl.
*A61N 1/36* (2006.01)
*G16H 50/20* (2018.01)

(52) U.S. Cl.
CPC ..... *A61N 1/36139* (2013.01); *A61N 1/36067* (2013.01); *G16H 50/20* (2018.01)

(58) Field of Classification Search
CPC .............. A61N 1/0529; A61N 1/36139; A61N 1/36067; G16H 50/20; A61B 2034/105; A61B 2034/107; A61B 2034/108; A61B 2090/3762; A61B 2576/023; A61B 34/10; A61B 5/0205; A61B 5/076; A61B 6/00; A61F 2/95; A61F 2002/30943; A61F 2240/004

See application file for complete search history.

(56) References Cited

U.S. PATENT DOCUMENTS

| | | |
|---|---|---|
| 11,712,564 B2 | 8/2023 | Miocinovic et al. |
| 2012/0203079 A1* | 8/2012 | McLaughlin ......... A61B 5/316 600/377 |
| 2016/0235323 A1* | 8/2016 | Tadi ..................... A61B 5/0006 |
| 2016/0256690 A1* | 9/2016 | Cecchi ............... A61N 1/36132 |

OTHER PUBLICATIONS

LeMoyne, Robert, Timothy Mastroianni. Applied Software Development with Python & Machine Learning by Wearable & Wireless Systems for Movement Disorder Treatment via Deep Brain Stimulation. World Scientific Publishing Co. Pte. Ltd., Sep. 2021.

(Continued)

*Primary Examiner* — Carl H Layno
*Assistant Examiner* — Anh-Khoa N Dinh
(74) *Attorney, Agent, or Firm* — Cislo & Thomas, LLP

(57) ABSTRACT

A system that amalgamates the domains of deep brain stimulation, wearable and wireless inertial sensor systems, machine learning, and multidisciplinary design optimization to achieve an optimal parameter configuration by automating the acquisition of an optimal parameter configuration for deep brain stimulation for movement disorders, such as essential tremor and Parkinson's disease, in a closed loop context. Wearable inertial sensors provide quantified feedback of movement disorder response to a deep brain stimulation parameter configuration. Using multidisciplinary design optimization, a minimal effective power, which is derived from tremor power and deep brain stimulation power, is acquired constituting an optimal parameter configuration.

20 Claims, 29 Drawing Sheets

(56) References Cited

OTHER PUBLICATIONS

LeMoyne, Robert, Timothy Mastroianni, Donald Whiting, and Nestor Tomycz. Wearable and Wireless Systems for Healthcare II: Movement Disorder Evaluation and Deep Brain Stimulation Systems. vol. 31. Springer, 2019.

LeMoyne, Robert, and Timothy Mastroianni. "An evolutionary perspective for Network Centric Therapy through wearable and wireless systems for reflex, gait, and movement disorder assessment with machine learning." In Wireless Sensor Networks-Design, Deployment and Applications. IntechOpen, Feb. 1, 2021.

LeMoyne, Robert, and Timothy Mastroianni. "Machine learning classification for Network Centric Therapy utilizing the multilayer perceptron neural network." In Multilayer Perceptrons: Theory and Applications, pp. 39-76. Nova Science Publishers, Mar. 2020.

LeMoyne, Robert, and Timothy Mastroianni. "Network Centric Therapy for wearable and wireless systems." In Smartphones: Recent Innovations and Applications, Chapter 7. Nova Science Publishers, 2019.

LeMoyne, Robert, Timothy Mastroianni, and N. Mohamudally. "Smartphone and portable media device: a novel pathway toward the diagnostic characterization of human movement." In Smartphones from an Applied Research Perspective. pp. 1-24. InTech, 2017.

LeMoyne, Robert, and Timothy Mastroianni. "Use of smartphones and portable media devices for quantifying human movement characteristics of gait, tendon reflex response, and Parkinson's disease hand tremor." In Mobile Health Technologies, pp. 335-358. Springer, 2015.

LeMoyne, Robert, Cristian Coroian, Timothy Mastroianni, Pawel Opalinski, Michael Cozza, and Warren Grundfest. "The merits of artificial proprioception, with applications in biofeedback gait rehabilitation concepts and movement disorder characterization." In Biomedical Engineering, pp. 165-198. InTech, 2009.

LeMoyne, Robert, Timothy Mastroianni, Donald Whiting, and Nestor Tomycz. "Distinction of an assortment of deep brain stimulation parameter configurations for treating Parkinson's disease using machine learning with quantification pf tremor response through a conformal wearable and wireless inertial sensor." Advances in Parkinson's Disease 9, No. 3 (Aug. 21, 2020): 21-39.

LeMoyne, Robert, Timothy Mastroianni, Donald Whiting, and Nestor Tomycz. "Preliminary Network Centric Therapy for machine learning classification of deep brain stimulation status for the treatment of Parkinson's disease with a conformal wearable and wireless inertial sensor." Advances in Parkinson's Disease 8, No. 04 (2019): 75-91.

LeMoyne, Robert, Timothy Mastroianni, Cyrus McCandless, Christopher Currivan, Donald Whiting, and Nestor Tomycz. "Implementation of a smartphone as a wearable and wireless accelerometer and gyroscope platform for ascertaining deep brain stimulation treatment efficacy of Parkinson's disease through machine learning classification." Advances in Parkinson's Disease 7, No. 2 (2018): 19-30.

LeMoyne, Robert. "Wearable and wireless accelerometer systems for monitoring Parkinson's disease patients-A perspective review." Advances in Parkinson's Disease 2013 (2013): 113-115.

LeMoyne, Robert, Timothy Mastroianni, Donald Whiting, and Nestor Tomycz. "Application of deep learning to distinguish multiple deep brain stimulation parameter configurations for the treatment of Parkinson's disease" In 2020 19th International Conference on Machine Learning and Applications (ICMLA'20), IEEE, Dec. 14, 2020.

LeMoyne, Robert, Timothy Mastroianni, Donald Whiting, and Nestor Tomycz. "Parametric evaluation of deep brain stimulation parameter configurations for Parkinson's disease using a conformal wearable and wireless inertial sensor system and machine learning." In 2020 42nd Annual International Conference of the IEEE Engineering in Medicine & Biology Society (EMBC), pp. 3606-3611. IEEE, Jul. 20, 2020.

LeMoyne, Robert, Timothy Mastroianni, Cyrus McCandless, Donald Whiting, and Nestor Tomycz. "Evaluation of machine learning algorithms for classifying deep brain stimulation respective of 'On' and 'Off' status." In 2019 9th International IEEE/EMBS Conference on Neural Engineering (NER), pp. 483-488. IEEE, 2019.

LeMoyne, Robert, Nestor Tomycz, Timothy Mastroianni, Cyrus McCandless, Michael Cozza, and David Peduto. "Implementation of a smartphone wireless accelerometer platform for establishing deep brain stimulation treatment efficacy of essential tremor with machine learning." In 2015 37th Annual International Conference of the IEEE Engineering in Medicine and Biology Society (EMBC), pp. 6772-6775. IEEE, 2015.

LeMoyne, Robert, Timothy Mastroianni, Michael Cozza, Cristian Coroian, and Warren Grundfest. "Implementation of an iPhone for characterizing Parkinson's disease tremor through a wireless accelerometer application." In 2010 Annual International Conference of the IEEE Engineering in Medicine and Biology, pp. 4954-4958. IEEE, 2010.

LeMoyne, Robert, Timothy Mastroianni, Donald Whiting, and Nestor Tomycz. "Deep learning for differentiating parameter configurations of deep brain stimulation for treating Parkinson's disease incorporating conformal wearable and wireless inertial sensors as an evolution for Network Centric Therapy." In Society for Neuroscience Global Connectome: A Virtual Event. 2021.

LeMoyne, Robert, Timothy Mastroianni, Donald Whiting, and Nestor Tomycz. "Network Centric Therapy for deep brain stimulation status parametric analysis with machine learning classification." In 49th Society for Neuroscience Annual Meeting (NanoSymposium). 2019.

LeMoyne, Robert, Timothy Mastroianni, Donald Whiting, and Nestor Tomycz. "Implementation of a smartphone as a wearable and wireless inertial sensor platform for determining efficacy of deep brain stimulation for Parkinson's disease tremor through machine learning." In 48th Society for Neuroscience Annual Meeting (NanoSymposium). 2018.

LeMoyne, Robert, Timothy Mastroianni, Nestor Tomycz, Donald Whiting, M. Oh, Cyrus McCandless, Christopher Currivan, and David Peduto. "Implementation of a multilayer perceptron neural network for classifying deep brain stimulation in 'On' and 'Off' modes through a smartphone representing a wearable and wireless sensor application." In 47th Society for Neuroscience Annual Meeting (featured in Hot Topics; top 1% of abstracts). 2017.

LeMoyne, Robert, Timothy Mastroianni, Nestor Tomycz, Donald Whiting, Cyrus McCandless, Christopher Currivan, David Peduto Cozza Michael. "I-Phone wireless accelerometer quantification of extremity tremor in essential tremor patient undergoing activated and inactivated deep brain stimulation." In 12th World Congress, International Neuromodulation Society's. 2015.

LeMoyne, Robert, Timothy Mastroianni, and Cristian Coroian. "Wireless accelerometer strategy for quantifying Parkinson's disease tremor" In 17th International Conference on Mechanics in Medicine and Biology. 2010.

LeMoyne, Robert, Timothy Mastroianni, Michael Cozza, Cristian Coroian, and Warren Grundfest. "Artificial proprioception for digital diagnostics." In 11th Annual UC Systemwide Bioengineering Symposium (Oral presentation). 2010.

LeMoyne, Robert, Cristian Coroian, and Timothy Mastroianni. "3D wireless accelerometer characterization of Parkinson's disease status." In Plasticity and Repair in Neurodegenerative Disorders. 2008.

LeMoyne, Robert; "Gradient optimized neuromodulation for Parkinson's disease." In 12th Annual UCLA Research Conference on Aging. 2007.

LeMoyne, Robert. "Multidisciplinary cost and performance optimization of a two stage liquid propulsion based launch vehicle." In 15th AIAA International Space Planes and Hypersonic Systems and Technologies Conference, 2008.

\* cited by examiner

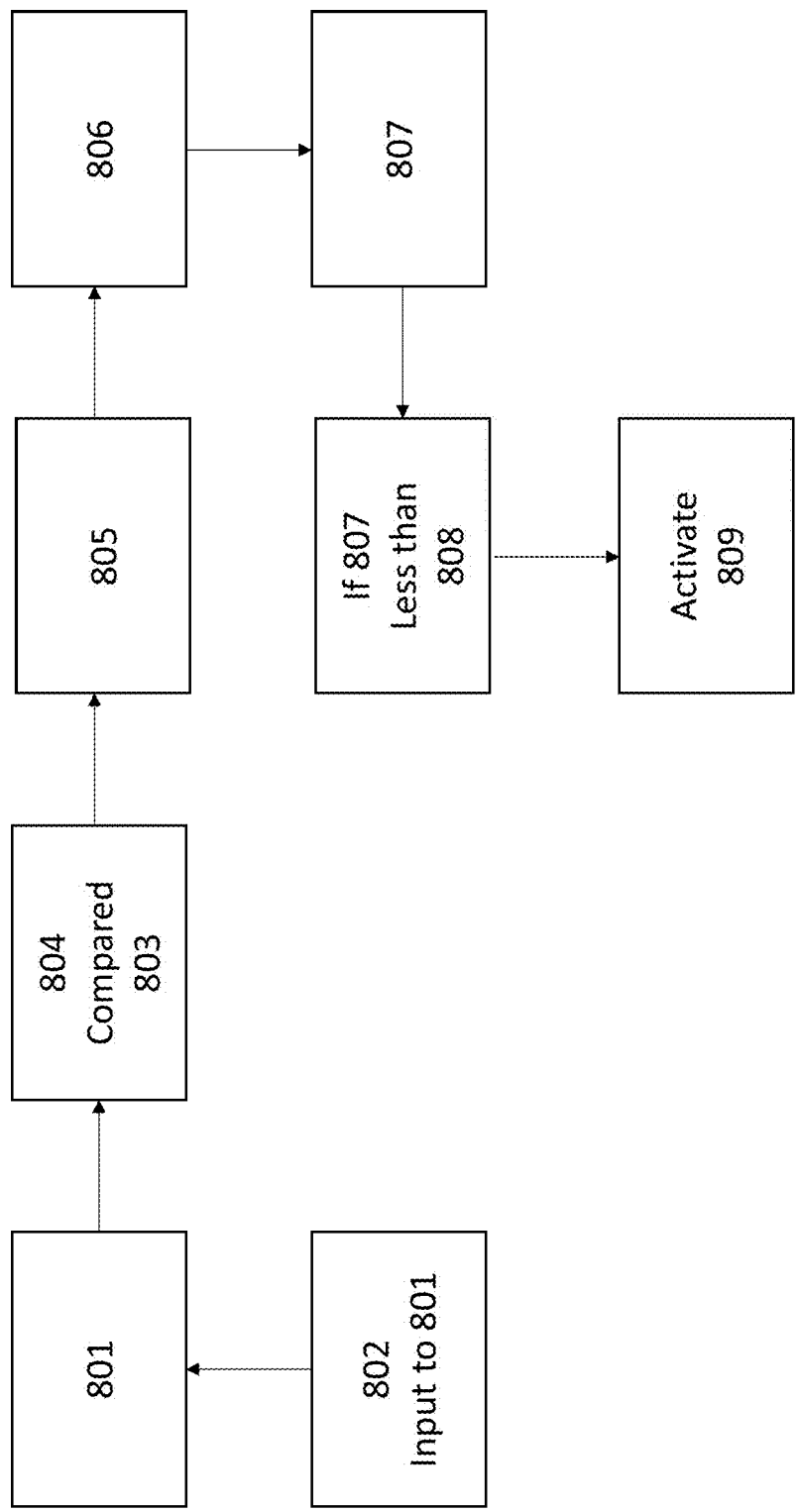

MULTIDISCIPLINARY DESIGN OPTIMIZATION OF NEUROMODULATION SYSTEMS

CROSS-REFERENCES TO RELATED APPLICATIONS

This application claims the benefit of Provisional Patent Application No. 63/221,438 filed on Jul. 13, 2021, which is incorporated herein in its entirety by this reference.

BACKGROUND OF THE INVENTION

Multidisciplinary Design Optimization ("MDO") is in the field of Aerospace and Mechanical Engineering. MDO has been applied in the advanced design optimization of launch vehicles. MDO inherently applies independent (input) variables that yield a dependent (output) variable. The dependent variable applies contrarian functions, such as for a launch vehicle performance estimating relationships and cost estimating relationships. For a launch vehicle an optimal costing launch vehicle may not produce optimal performance, and the optimal performance may not yield an optimal cost. However, when combining performance per cost to a dependent variable function, a series of independent variables can achieve an optimal configuration through MDO.

Multidisciplinary design optimization may be interpreted as a numerical optimization process, wherein an independent variable or series of independent variables achieves an optimal configuration that produces the most desirable or efficient result with, for example, minimal value for the dependent variable (e.g., power, energy, time, resources, effort, money, etc.). For a launch vehicle the dependent variable can be prescribed as performance (payload to orbit) per cost of launch vehicle, and associated independent variables can be prescribed as rocket specific impulse and launch vehicle initial mass. The design space defining the dependent variable can be defined by a complex series of performance estimation relationships and cost estimating relationships. Applying MDO, the optimal launch configurations can be determined to produce the most efficient performance (sending payload to space at a minimal cost). For multidisciplinary design optimization that optimizes by achieving a minimal, the reciprocal of the dependent variable can be applied, such as cost per payload to orbit. The multidisciplinary design optimization minimal for the reciprocal of the dependent variable, such as cost per payload to orbit, has the corresponding effect of achieving a maximal payload to orbit per cost.

MDO can be applied to the field of neuroscience, and in particular, neuromodulation systems for treatment of neurological disorders. By way of example only, the advent of deep brain stimulation, which is a type of neuromodulation system, has considerably influenced the quality of life for persons with movement disorders, such as Parkinson's disease and essential tremor. However, a notable challenge still persists with the issue of achieving an optimal deep brain stimulation parameter configuration, which can even protract to on the order of months to achieve an optimal deep brain stimulation parameter configuration. The global objective is to establish a conclusive pathway to realizing closed-loop optimization of deep brain stimulation for people with movement disorders, such as Parkinson's disease and essential tremor through a highly novel technological amalgamation incorporating conformal wearable and wireless inertial sensor systems, machine learning for distinguishing deep brain stimulation response, and design optimization, which inherently derives from the domain of rocket science.

Quantifying the response to a deep brain stimulation parameter configuration is imperative for the optimization process. Inertial sensors constitute a foundation to the deep brain stimulation parameter configuration optimization process, since the inertial signal data can objectively quantify the deep brain stimulation parameter configuration for a person with a movement disorder, such as Parkinson's disease and essential tremor. The inherent utility of wearable inertial sensor systems for quantifying tremor with regards to deep brain stimulation has been identified in multiple research publications for quantifying response of deep brain stimulation.

LeMoyne et al. have extensively researched, developed, tested, and evaluated the conformal wearable and wireless inertial sensor system for the quantification of response to deep brain stimulation parameter configurations for movement disorders relevant to the domain of essential tremor and Parkinson's disease. In particular, the inertial sensor signal data has been successfully post-processed and consolidated into feature sets for machine learning, which has yielded considerable classification accuracy to distinguish between the parameter configuration scenarios.

The utility of machine learning for deep brain stimulation treatment of movement disorders is represented by the ability to derive an objectively distinct computer-derived and automated diagnosis, such as the determination that the patient specific conditions warrant the implementation of the optimization process. LeMoyne et al. have successfully implemented wearable and wireless inertial sensor systems for the quantification of movement disorders, such as Parkinson's disease and essential tremor response to deep brain stimulation tuning status while augmented through the distinction of machine learning classification. The next evolution involves the incorporation of multidisciplinary design optimization intrinsic to the domain of rocket science for achieving an optimal deep brain stimulation parameter configuration, for which with the scope of the invention shall be demonstrated through single variable design optimization of the deep brain stimulation amplitude parameter.

SUMMARY OF THE INVENTION

The invention of the present application can solve this problem by applying multidisciplinary design optimization to neuromodulation systems. For a perspective of multidisciplinary design optimization, consider the model design space to be the series of complex formulas to realize a launch vehicle configuration through multiple disciplines, such as performance estimation relationships and cost estimation relationships. The model design space is distilled to dependent variable for optimization, such as performance per cost, with the goal of minimizing the cost of the launch vehicle while maximizing performance, such as pounds of payload to lower Earth orbit. The independent variables can be constrained by maximal and minimal limits, such as specific impulse (propulsion propellant economy) and launch vehicle initial mass. Multidisciplinary design optimization then achieves an optimal dependent variable based on the available constraints of the independent variables and the respective model design space.

With respect to multidisciplinary design optimization of an optimal parameter configuration for deep brain stimulation regarding movement disorders, such as Parkinson's disease and essential tremor, the model design space is the unique brain of the subject with a movement disorder, such as Parkinson's disease and essential tremor. The independent variables are the available parameter configurations. The dependent variable to be optimized (effective power) is a concatenation of tremor power derived from the conformal wearable and wireless inertial sensor system and the stimulation power derived from the deep brain stimulation parameter configurations available per clinically prescribed constraints.

For successful implementation of multidisciplinary design optimization, the establishment of a prudent dependent variable is imperative. Effective power, which is optimized, is a function of inertial signal derived tremor power and deep brain stimulation (DBS) power. Tremor power and DBS power are intentionally selected based on their properties. Maximal DBS power elicits minimal tremor power, and minimal DBS tremor power elicits maximal tremor power. Intuitively, the optimal power derived according to the effective power resides within the clinically constrained bounds of the parameter configurations that establish maximal and minimal DBS power.

Embodiments of multidisciplinary design optimization of neuromodulation systems incorporate independent variables defining the stimulation characteristics of the neuromodulation system, such as amplitude, pulse width, stimulation frequency, and polarity with respect to deep brain stimulation. The dependent variable, for which a multidisciplinary design optimization achieves a minimal value in a neuromodulation setting (e.g., deep brain stimulation treatment of a movement disorder, such as Parkinson's disease) can be prescribed as an effective power (combination of tremor power and Deep Brain Stimulation Power). The design space defining the dependent variable can be defined as the quantified response resultant of therapeutic intervention provided by a neuromodulation system, such as deep brain stimulation, to brain of the subject being treated.

MDO for a neuromodulation system has a performance function, such as therapeutic response, and a cost function, such as battery output. Therefore, MDO for a neuromodulation system can achieve an optimal performance per cost, or performance times cost based on parameter configurations. The dependent variable can be represented by the performance per cost, and the independent variable is represented by the parameter configuration of the deep brain stimulation. In some embodiments, the dependent variable can be represented by the performance times cost, and the independent variable is represented by the parameter configuration.

The dependent variable can be optimized based on the independent variable, wherein the dependent variable represents performance per cost or performance times cost, wherein performance can be interpreted as a function of neuromodulation efficacy, such as tremor power, and wherein cost can be interpreted as a function of the electrical power imparted by the neuromodulation system.

Essentially, the optimal independent variable or independent variable set, such as a neuromodulation parameter configuration (amplitude, pulse width, frequency, polarity, etc. of the stimulation), achieves through MDO maximal performance, such as minimal tremor, in conjunction with minimal cost, such as minimal neuromodulation electrical power. For the scenario described in this paragraph, the optimized dependent variable, such as in the context of neuromodulation parameter configuration, which are the corresponding independent variables, the minimal tremor power can be achieved by a parameter configuration that imparts minimal electrical power required from the neuromodulation system. Such an optimized parameter configuration would provide a subject treated by the neuromodulation system with the optimal utility of maximal tremor suppression in conjunction with maximal battery life duration (or minimal power usage).

Representative embodiments of optimization algorithms can be used for achieving the effect of multidisciplinary design optimization to ascertain the optimal independent variable or independent variable set that achieves an optimal dependent variable based on the respective design space. Representative embodiments of optimization algorithms include, but are not limited to: gradient-based methods (Adjoint equation, Newton's method, Steepest descent, Conjugate gradient, Sequential quadratic programming); gradient-free methods (Hooke-Jeeves pattern search, Nelder-Mead method); population-based methods (Genetic algorithm, Memetic algorithm, Particle swarm optimization, Harmony search, Open Source Development Model Algorithm (ODMA)); and other methods (Random search, Grid search, Simulated annealing, Direct search, and Indirect Optimization based on Self-Organization (IOSO)).

Regarding the application of multidisciplinary design optimization for the optimization of a launch vehicle, the design space is based on a complex set of performance estimating relationships and cost estimating relationships. Regarding the application of multidisciplinary design optimization for the optimization of a deep brain stimulation parameter configuration, the design space is based on the response of the brain for the quantified tremor suppression for a movement disorder.

Wearable and wireless systems can be used to quantify the response to therapeutic intervention of neuromodulation, such as deep brain stimulation. The resultant wearable and wireless system signal data can be consolidated to a feature set for machine learning classification to establish distinction (computer automated diagnosis) of therapeutic response in a patient specific context.

The domain of neuromodulation spans a multitude of therapeutic interventions, for which electrical stimulation of the brain improves the health status of the subject. Representative exemplars of neuromodulation systems are: Deep brain stimulation (DBS), such as for the treatment of Parkinson's disease, essential tremor, and dystonia; Stimulation of peripheral nervous system, such as vagus nerve stimulation (VNS); and Non-invasive brain stimulation, such as transcranial Direct Current Stimulation (tDCS).

Wearable systems for quantifying the response of a neuromodulation system, such as deep brain stimulation, can be provided by the signal provided by inertial sensors. Other embodiments of wearable systems for quantifying the response of neuromodulation systems pertain to a wearable system that can provide signal data to quantify the characteristics of the neuromodulation system's therapeutic benefit to a subject and also the potentially adverse response can also be used.

Additional embodiments of machine learning, including deep learning, pertain to computer automated diagnostic means of applying quantified feedback, such as from a neuromodulation system, to provide distinguishing medical and/or clinical situational awareness.

The global methodology encompassed by the multidisciplinary design optimization of neuromodulation systems utilizes the quantification of the response of a therapeutic intervention from a neuromodulation system, such as with a wearable system. Applications of machine learning, or a representative embodiment, include to diagnose the need to initiate MDO to achieve a global optimal of performance per cost or performance times cost (dependent variable) based on a series of independent variables, such as the parameter configurations. Upon the convergence of the multidisciplinary design optimization of neuromodulation system, an optimal independent variable or series of independent variables, such as a deep brain stimulation system parameter configuration, achieves an optimized dependent variable, such as a minimal effective power as a function of tremor power and DBS power.

Implementation of the global methodology realizes the capability for anyone skilled in the art to reduce to practice a viable methodology for closed loop optimization of neuromodulation systems in conjunction with MDO.

For example, the deep brain stimulation amplitude parameter configuration can be selected as the independent design variable for optimization of the effective power. In essence, the amplitude can derive the DBS power. The tremor power can be derived from tremor power based on the inertial sensor signal data measured by the conformal wearable and wireless inertial sensor system through an evaluation suitable to measure tremor for a person with a movement disorder in conjunction with the deep brain stimulation system amplitude setting.

Future embodiments can be extrapolated to a more complex model design space. The available four parameter configuration for deep brain stimulation, such as amplitude, stimulation frequency, pulse width, and polarity, can be applied to derive the DBS power, which can subsequently yield an associated tremor power implemented through quantification of the prescribed evaluation suitable to measure tremor for a person with a movement disorder based on the inertial signal data quantified by the conformal wearable and wireless inertial sensor system. The multidisciplinary design optimization derived optimal power based on the effective power may ascertain the optimal deep brain stimulation parameter configuration for amplitude, stimulation frequency, pulse width, and polarity from within the bounds of their clinically prescribed constraints. Embodiments for multidisciplinary design optimization of the deep brain stimulation parameter configuration for the treatment of movement disorders, such as Parkinson's disease and essential tremor, can achieve fully automated and closed-loop acquisition of the optimal parameter configuration.

In summary, the realization of multidisciplinary design optimization is a breakthrough pathway for the automated and closed-loop optimization of a patient specific deep brain stimulation parameter configuration for a person with a movement disorders, such as Parkinson's disease and essential tremor.

BRIEF DESCRIPTION OF THE DRAWINGS

FIGS. 8a and 8b show representations of a process for machine learning classification.

DESCRIPTION OF THE PREFERRED EMBODIMENTS

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

The invention of the present application is directed towards the method and system for achieving optimal neuromodulation parameter configurations using a wearable system that measures a response to a neuromodulation intervention (such as deep brain stimulation, peripheral nerve stimulation, non-invasive neural stimulation, and the like), and a computer system to execute a multidisciplinary design optimization process to optimize the neuromodulation parameter configuration for achieving a desired result, such as maximum efficiency. The computer system can be configured for machine learning to diagnose the need to activate the multidisciplinary design optimization process.

Deep brain stimulation occurs by implanting an electrode into a desired region of the brain, such as the ventral intermediate nucleus (VIM) and subthalamic nucleus (STN)

which are frequently utilized targets. The electrodes are connected to an implantable pulse generator. The implantable pulse generator can be operatively connected to the computer system, such as a clinical programmer, and configured with the desired neuromodulation parameter configuration.

Preliminary Data

Preliminary data has been demonstrated through the use of smartphones as functionally wearable and wireless inertial sensor system. The inertial signal data recording the movement disorder during an evaluation suitable to measure tremor for a person with a movement disorder was post-processed into a feature set for machine learning classification, and for Parkinson's disease the inertial signal data recording pertained to resting tremor, which was then post-processed into a feature set for machine learning classification. Considerable machine learning classification was able to distinguish between deep brain stimulation set to 'On' status and 'Off' status for subjects with movement disorder.

Figure 5:
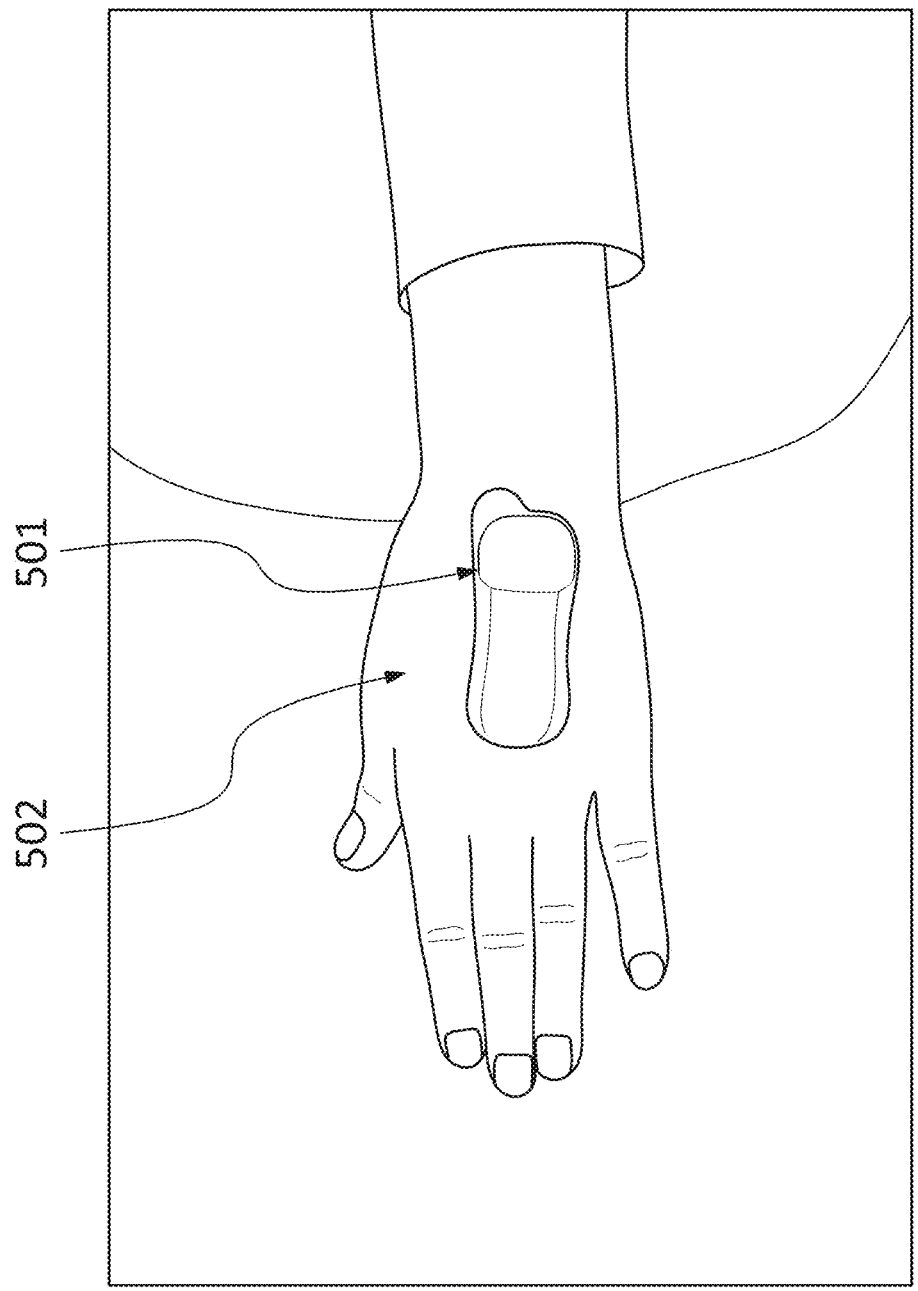
FIG. 5 shows and embodiment of the conformal wearable and wireless inertial sensor system mounted about the dorsum of the hand.

Research has been successfully conducted for deep brain stimulation for subjects with Parkinson's disease using the conformal wearable and wireless inertial sensor system, which was mounted to the dorsum of the hand as presented in FIG. 5, to quantify the response with respect to an assortment of deep brain stimulation amplitude parameter settings. Other sensors, such as optical sensors (e.g., a motion sensor, a motion detector, a camera sensor, an image sensor, and the like), magnetic sensors (e.g., electromagnetic systems), and any other sensors that can detect motion or movement can be used. Sensors that possess the characteristic ability to quantify the response to a neuromodulation system's parameter configuration by measuring and recording the sensor data can be used. Depending on the type of sensor used, the sensor need not be wearable by the user.

Figure 6A:
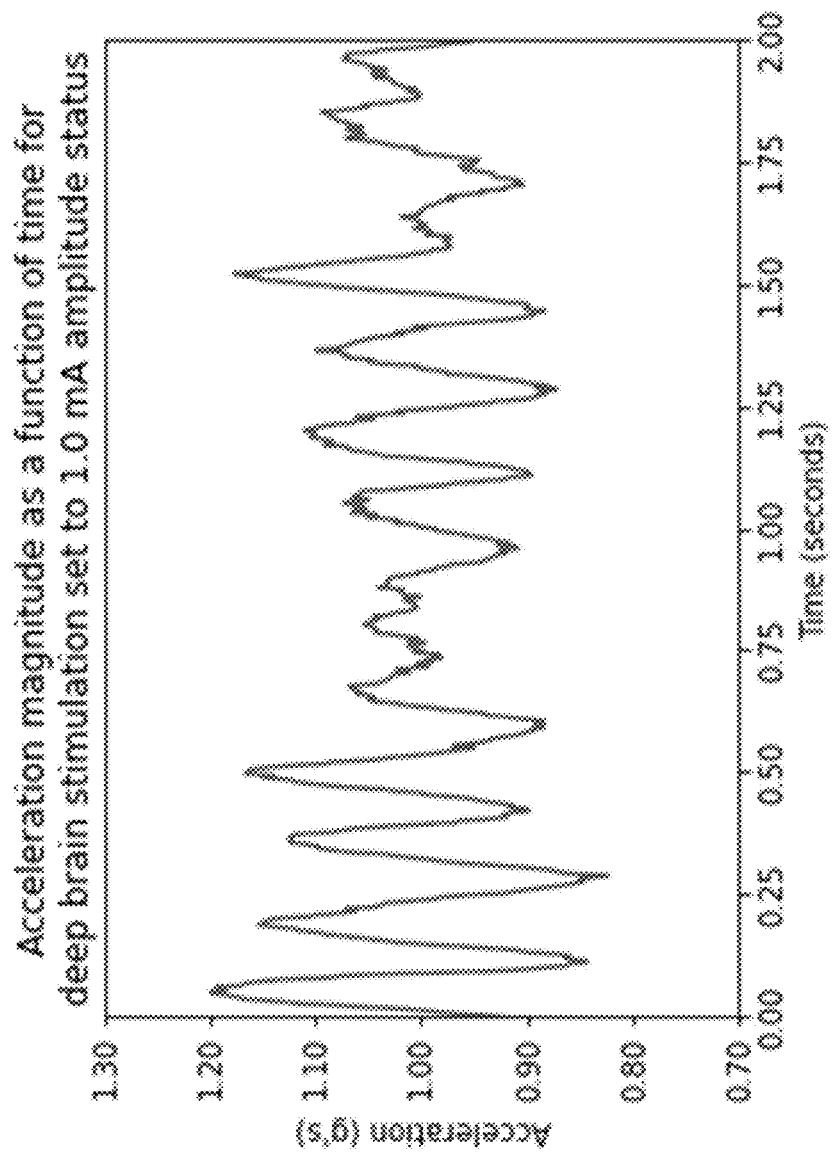
FIGS. 6a to 6e show graphs of an accelerometer signal for subject with Parkinson's disease hand tremor recorded by conformal wearable and wireless inertial sensor system.
Figure 6B:
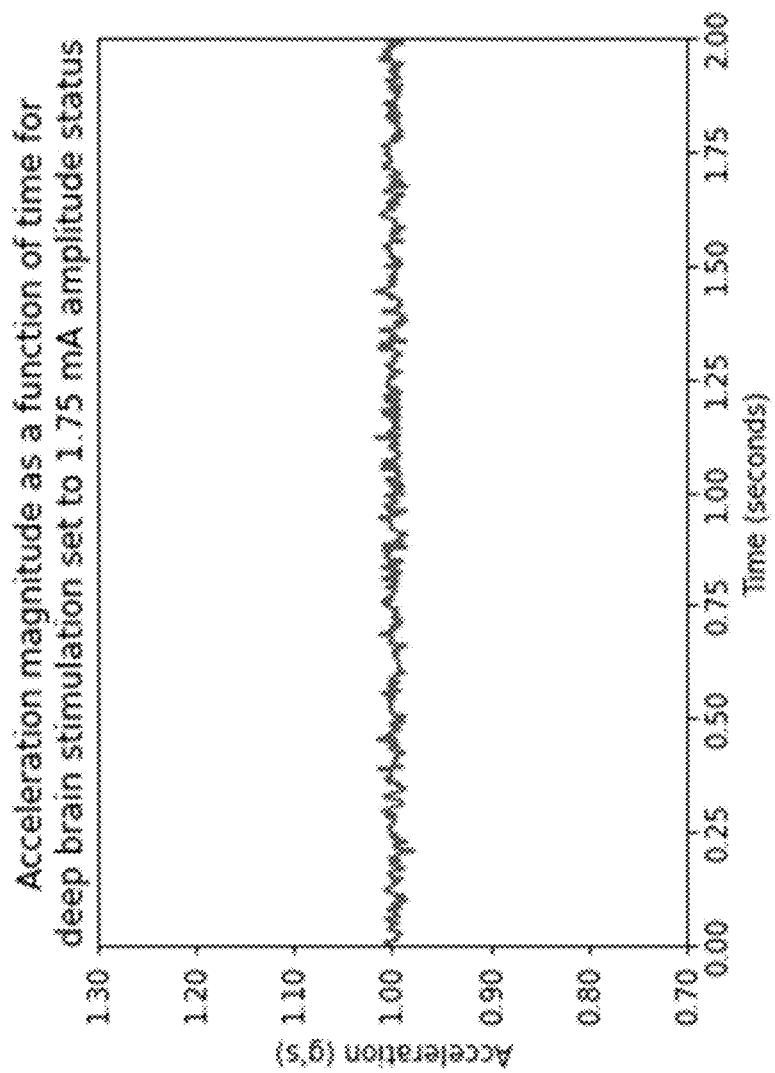
Figure 6C:
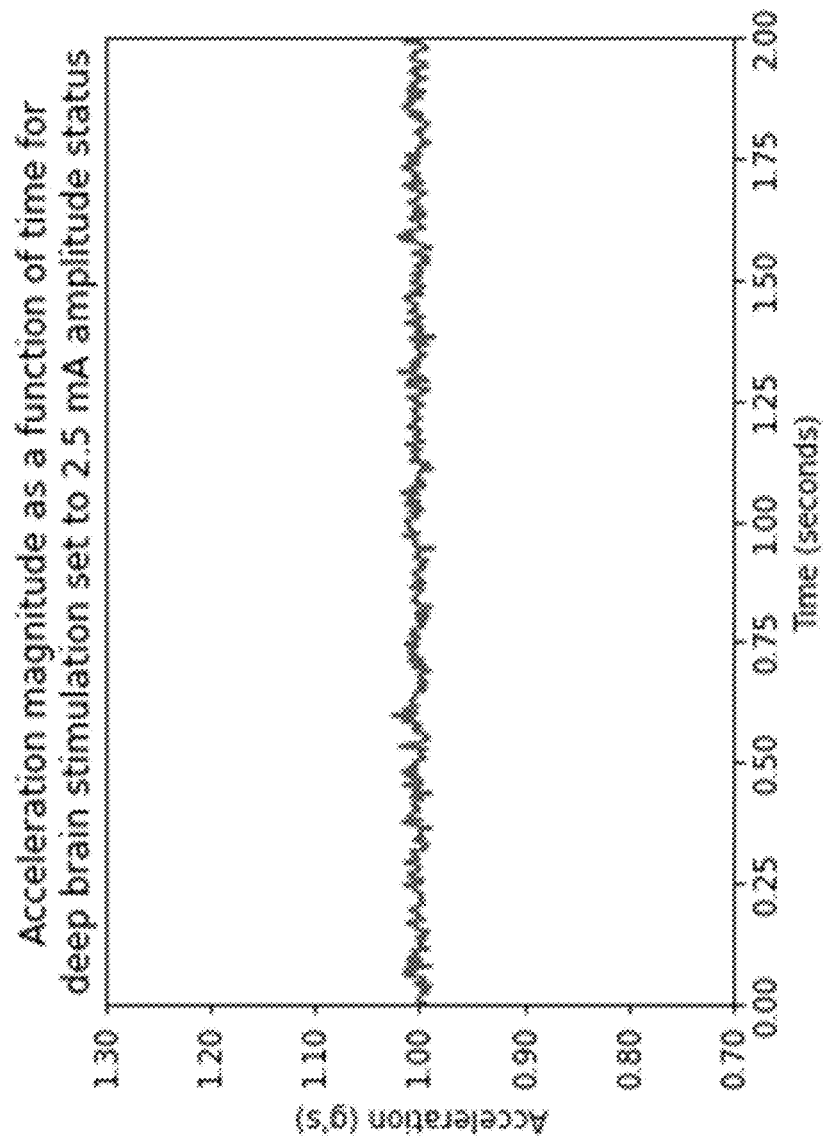
Figure 6D:
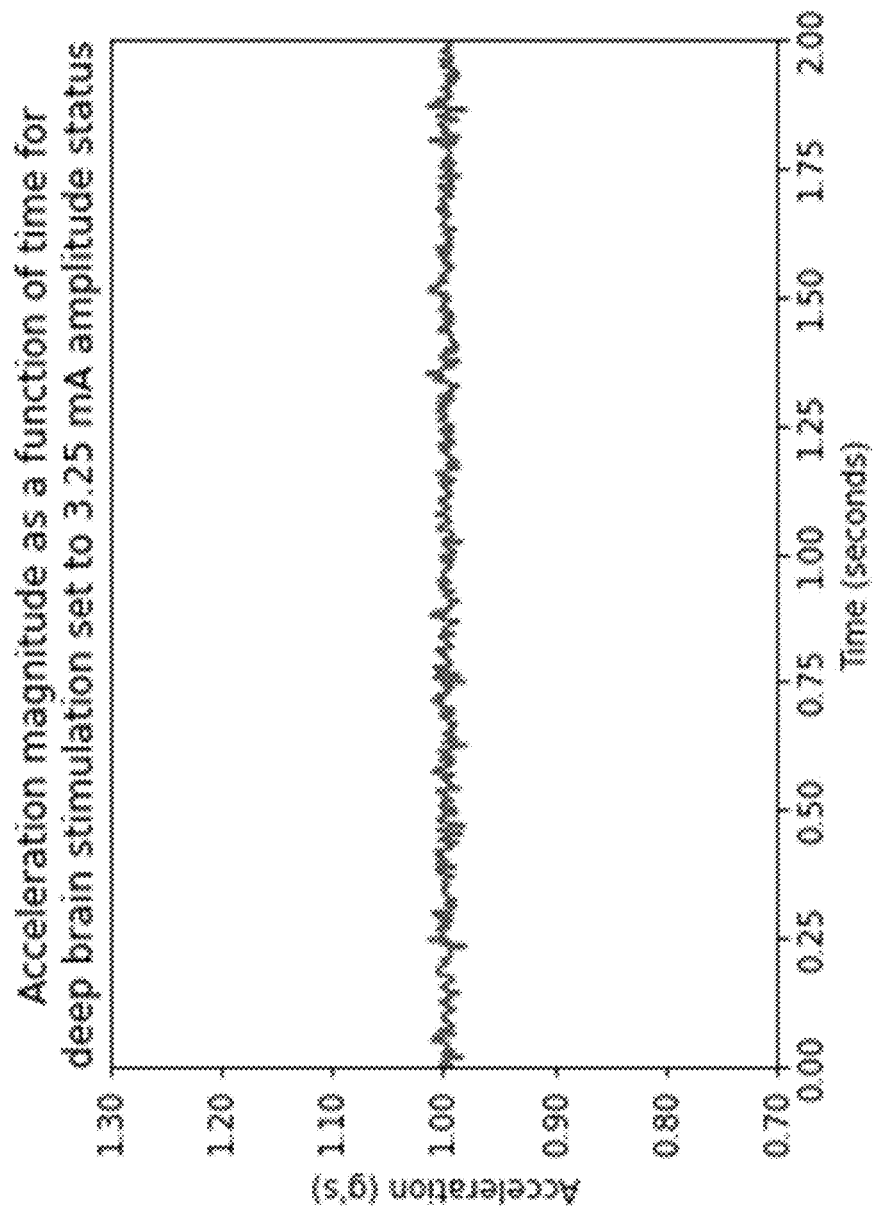
Figure 6E:
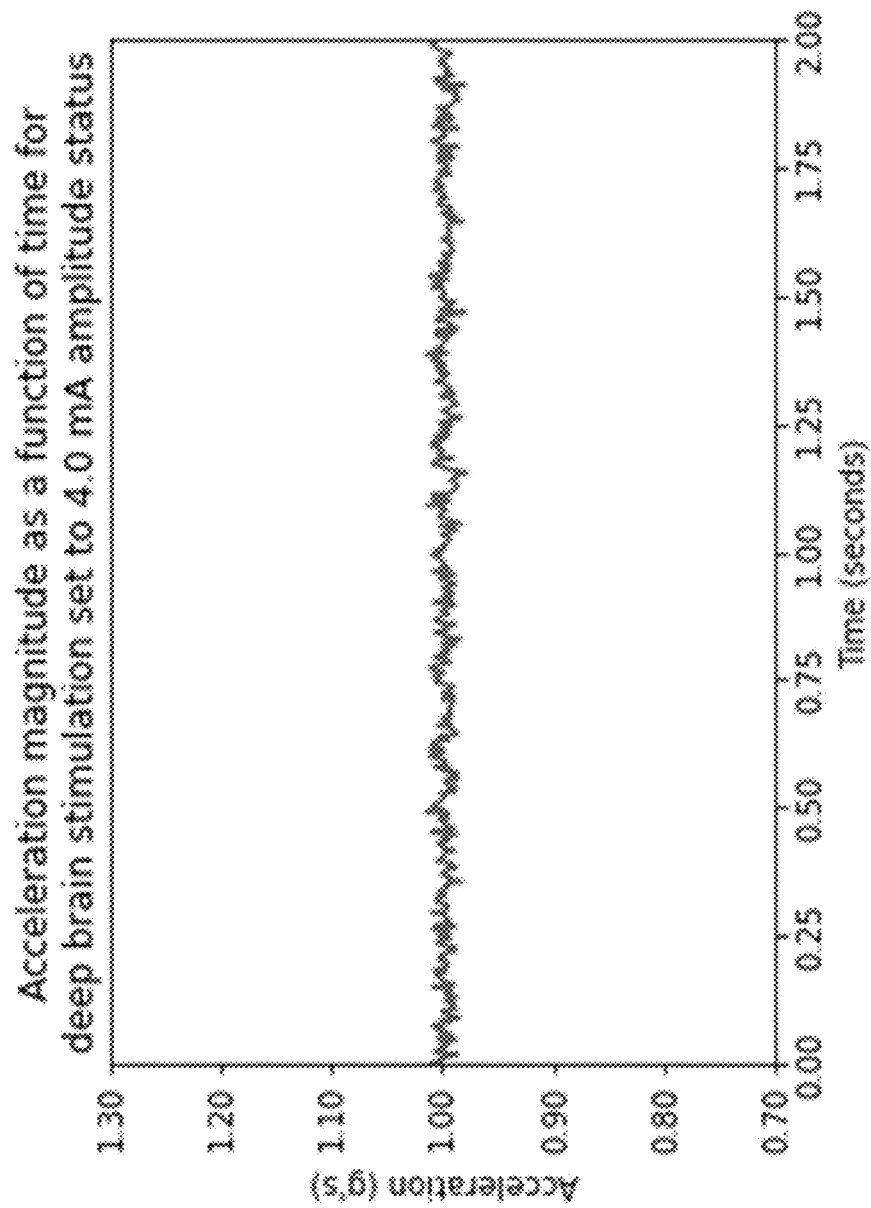

The resultant machine learning and deep learning classification achieved considerable classification accuracy for distinguishing the deep brain stimulation amplitude parameter settings based on the quantified inertial sensor signal data obtained by the conformal wearable and wireless inertial sensor system. FIGS. 6a to 6e present a representative accelerometer signal recording (measured in terms of gravitational acceleration) of the evaluation suitable to measure tremor for a person with a movement disorder with respect to deep brain stimulation set to an assortment of amplitude parameter settings. In FIG. 6a, the acceleration magnitude is plotted as a function of time for deep brain stimulation set to 1.0 mA amplitude status. In FIG. 6b, the acceleration magnitude is plotted as a function of time for deep brain stimulation set to 1.75 mA amplitude status. In FIG. 6c, the acceleration magnitude is plotted as a function of time for deep brain stimulation set to 2.5 mA amplitude status. In FIG. 6d, the acceleration magnitude is plotted as a function of time for deep brain stimulation set to 3.25 mA amplitude status. In FIG. 6e, the acceleration magnitude is plotted as a function of time for deep brain stimulation set to 4.0 mA amplitude status.

With the ability to distinguish between various deep brain stimulation parameter configurations, the next phase of the evolution envisions the optimization of actual deep brain stimulation parameters. Multidisciplinary design optimization possesses the capability to simultaneously optimize deep brain stimulation parameter configurations based on the subject's quantified response based on a conformal wearable and wireless inertial sensor system. The present invention is to apply multidisciplinary design optimization for the primary deep brain stimulation parameter configuration (e.g., amplitude, frequency, pulse width, polarity, and the like) with regards to subjects with movement disorders, such as Parkinson's disease and essential tremor, in the representative context of multidisciplinary design optimization. Additionally, the present invention enables one skilled in the art to apply multidisciplinary design optimization to any domain of neuromodulation systems that incorporate a quantified means of feedback.

The domain of neuromodulation spans a multitude of therapeutic interventions, for which electrical stimulation of the nervous system improves the health status of the subject. Representative exemplars of neuromodulation systems are: Deep brain stimulation (DBS), such as for the treatment of Parkinson's disease, essential tremor, and dystonia; Stimulation of peripheral nervous system, such as vagus nerve stimulation (VNS); and non-invasive brain stimulation, such as transcranial Direct Current Stimulation (tDCS).

Acquisition of Signal Data in Incremental Methodology with Time Stepping for Real Time Applications A general process for acquiring the response to a neuromodulation system, such as deep brain stimulation for the treatment of Parkinson's disease, through a wearable, such as a conformal wearable inertial sensor, capable of acquiring quantified signal data of the neuromodulation system response is presented. The current demonstration involves clinical supervision for manually modifying the deep brain stimulation parameter configuration, such as the amplitude. Embodiments can apply autonomously incrementally varied parameter configuration within a set of bounds prescribed by the clinical supervision. The autonomous mode can incorporate sufficient temporal delay for the subject to adjust to the new incrementally varied parameter configuration. Other embodiments may incorporate random modifications, such as amplitude, of the incrementally varied parameter configurations.

The process of the present invention comprises securing a wearable to the hand (e.g., on the dorsum), activating (e.g., wirelessly) the wearable for acquiring the inertial sensor signal data with subsequent transmission of the signal data to a computing resource for storage (such as the cloud or other remote computers or servers), and modifying the deep brain stimulation clinical programmer to a set parameter configuration. By way of example only, the following parameter configuration scenarios can be used: stimulation amplitude with prescribed upper bound (4.0 mA) and lower bound (1.0 mA) of a predetermined independent variable, such as amplitude, and predetermined number of increments (e.g., 5) that can be manually (clinically) modified or incremented in a real time increment to achieve the following effect: deep brain stimulation set to amplitude 1.0 mA, deep brain stimulation set to amplitude 1.75 mA, deep brain stimulation set to amplitude 2.5 mA, deep brain stimulation set to amplitude 3.25 mA, and deep brain stimulation set to amplitude 4.0 mA.

The wearable can be a conformal wearable. Alternative embodiments can apply the wearable to a more representative aspect of the human anatomy with respect to the neuromodulation response being measured. Wearables can be worn or otherwise attached to the user with known techniques.

Machine Learning Classification

Some embodiments of the present invention involve the application of machine learning. Machine learning serves the role of activating the MDO neuromodulation process. Machine learning serves the role of computer automated diagnostics for determining the need to activate the MDO neuromodulation process. In the preferred embodiment, wearable inertial sensors provide the basis for the machine learning feature set. For example, if the classification accuracy (defined as correctly classified instances divided by total number of instances) of the current status of the subject treated by neuromodulation, such as deep brain stimulation, falls below a prescribed threshold, such as achieving a classification accuracy of less than 75% relative to a prescribed baseline, the MDO process for the neuromodulation system could then be initiated.

Any available machine learning algorithm, such as J48 Decision Tree, k-Nearest Neighbors, and the Multilayer Perceptron Neural Network, inclusive of a machine learning algorithm capable of achieving the effect of a classification accuracy based on quantified feedback regarding the response to a neuromodulation parameter configuration would be appropriate. Alternative embodiments are inclusive of artificial intelligent algorithms capable of providing classification accuracy with respect to the quantified wearable signal data response to a neuromodulation parameter configuration, such as deep learning.

Another alternative embodiment would be for the continuous operation of the MDO neuromodulation process, or the activation of the MDO neuromodulation process in accordance with a time incremented manner.

Multidisciplinary Design Optimization Phase (a Pathway for Closed-Loop Optimization)

Embodiments of the present invention incorporate independent variables defining the stimulation characteristics of the neuromodulation system, such as with respect to deep brain stimulation amplitude, pulse width, stimulation frequency, and polarity. The dependent variable, for which a multidisciplinary design optimization achieves a minimal, such as for deep brain stimulation treatment of a movement disorder, such as Parkinson's disease, can be prescribed as an effective power (combination of tremor power and DBS Power). The design space defining the dependent variable can be defined as the quantified response resultant of therapeutic intervention provided by a neuromodulation system, such as deep brain stimulation, to the brain of the subject being treated. In some embodiments, peripheral nerve stimulation and non-invasive neural stimulation can also be used.

Multidisciplinary Design Optimization of Neuromodulation System can have a performance function, such as therapeutic response, and a cost function, such as battery output. Therefore, MDO for a neuromodulation system can achieve an optimal performance per cost or performance times cost based on parameter configurations. The dependent variable can be represented by the performance per cost, and the independent variable is represented by the parameter configuration. In some embodiments, the dependent variable can be represented by the performance times cost, and the independent variable can be represented by the parameter configuration.

The dependent variable is to be optimized based on the independent variable, wherein the dependent variable represents performance per cost or performance times cost, wherein performance can be interpreted as a function of neuromodulation efficacy, such as tremor power, and wherein cost can be interpreted as a function of the electrical power imparted by the neuromodulation system.

Essentially, the optimal independent variable or independent variable set, such as a neuromodulation parameter configuration, achieves through MDO maximal performance, such as minimal tremor, in conjunction with minimal cost, such as minimal neuromodulation electrical power. For the scenario described in this paragraph, the optimized dependent variable, such as the neuromodulation parameter configuration, the minimal tremor power is achieved by a parameter configuration that imparts minimal electrical power required from the neuromodulation system. Such an optimized parameter configuration would provide a subject treated by the neuromodulation system with the optimal utility of maximal tremor suppression in conjunction with maximal battery life duration.

Representative embodiments of optimization algorithms for achieving the effect of multidisciplinary design optimization ascertain the optimal independent variable or independent variable set that achieves an optimal dependent variable based on the respective design space. Representative embodiments of optimization algorithms are inclusive of: Gradient-based methods (e.g., Adjoint equation, Newton's method, Steepest descent, Conjugate gradient, Sequential quadratic programming); Gradient-free methods (e.g., Hooke-Jeeves pattern search, and Nelder-Mead method); Population-based methods (e.g., Genetic algorithm, Memetic algorithm, Particle swarm optimization, Harmony search, and ODMA); and other methods (Random search, Grid search, Simulated annealing, Direct search, and Indirect Optimization based on Self-Organization (IOSO)).

Regarding the application of multidisciplinary design optimization for the optimization of a launch vehicle, the design space is based on a complex set of performance estimating relationships and cost estimating relationships. Regarding the application of multidisciplinary design optimization for the optimization of a deep brain stimulation parameter configuration, the design space is based on the response of the brain for the quantified tremor suppression for a movement disorder.

Wearable and wireless systems quantify the response to therapeutic intervention. The resultant wearable and wireless system signal data can be consolidated to a feature set for machine learning classification to establish distinction (computer automated diagnosis) of therapeutic response in a patient specific context. In some embodiments, signal data can be collected by other types of sensors. In some embodiments, the sensors need not be wearable.

The domain of neuromodulation spans a multitude of therapeutic interventions, for which electrical stimulation of the brain improves the health status of the subject. Representative exemplars of neuromodulation systems are: Deep brain stimulation (DBS), such as for the treatment of Parkinson's disease, essential tremor, and dystonia; Stimulation of peripheral nervous system, such as vagus nerve stimulation (VNS); and Non-invasive brain stimulation, such as transcranial Direct Current Stimulation (tDCS).

Wearable systems for quantifying the response of a neuromodulation system, such as deep brain stimulation, can be provided by the signal provided by inertial sensors. Other embodiments of wearable systems for quantifying the response of neuromodulation systems pertain to a wearable system that can provide signal data to quantify the characteristics of the neuromodulation system's therapeutic benefit to a subject and also the potentially adverse response.

Additional embodiments of machine learning, including, but not limited to, deep learning, pertain to computer automated diagnostic means of applying quantified feedback, such as from a neuromodulation system, to provide distinguishing medical and/or clinical situational awareness.

The global methodology encompassed by the multidisciplinary design optimization of neuromodulation systems requires a means of quantifying the response of a therapeutic intervention from a neuromodulation system, such as a wearable system. Application of machine learning, or a representative embodiment, can be used to diagnose the need to initiate MDO to achieve a global optimal of performance per cost or performance times cost (dependent variable) based on a series of independent variables, such as the parameter configurations. Upon the convergence of the multidisciplinary design optimization of neuromodulation system, an optimal independent variable or series of independent variables, such as a deep brain stimulation system parameter configuration, achieves an optimized dependent variable, such as a minimal effective power as a function of tremor power and DBS power.

Implementation of the global methodology realizes the capability for anyone skilled in the art to reduce to practice a viable methodology for closed loop optimization of neuromodulation systems in conjunction with MDO.

In some embodiments, the optimized dependent variable is derived from a minimal dependent variable as a function of a confluence of established performance parameters raised to a first exponent, and confluence of established cost parameters raised to a second exponent, such that exponential powers of the confluence of established performance parameters and confluence of established cost parameters sum to 1. In some embodiments the exponential powers of the confluence of established performance parameters and confluence of established cost parameters can be modulated per the discretion of the supervising operator.

The scope of the multidisciplinary design optimization phase (a pathway for closed-loop optimization) emphasizes deep brain stimulation. Alternative embodiments are inclusive of neuromodulation systems with parameter configurations (independent variables) and quantified response by wearable signal data in conjunction with power consumption cost of parameter configurations (dependent variable). The multidisciplinary design optimization phase can derive the optimal amplitude setting for a respective parameter configuration. The scope of the multidisciplinary design optimization phase can be used solely to identify the optimal amplitude settings. In alternative embodiments, the multidisciplinary design optimization phase can optimize the amplitude, stimulation frequency, pulse width, polarity, or any combination thereof, which would considerably increase the complexity of this study. The optimization of the amplitude establishes a precedent for alternative embodiments for the multidisciplinary design optimization of deep brain stimulation amplitude, stimulation frequency, pulse width, and polarity.

A representative of multidisciplinary design optimization incorporates an independent variable (e.g., amplitude) and a dependent variable (e.g., effective power). In the case of launch vehicle design optimization, the dependent variable is arranged to maximize performance (payload to orbit) and minimize cost (cost of launch vehicle). The multidisciplinary design optimization minimizes effective power in terms of a concatenation of tremor power and deep brain stimulation amplitude-derived power.

The tremor power can be derived from accelerometer and/or gyroscope signal data acquired during the evaluation suitable to measure tremor for a person with a movement disorder. Other motion sensors can also be used, including image sensors, magnetic sensors, and any other sensor capable of measuring and recording the characteristics of movement can be suitable. The tremor power (e.g., based on the multiplication of mass, acceleration less gravity offset, and velocity) during the evaluation suitable to measure tremor for a person with a movement disorder can be computed as a function of anthropomorphic derived hand mass (m), tremor maximal acceleration signal (a), acceleration of gravity (g), and derived velocity in temporal coherence with the maximal acceleration signal (a) in terms of the gyroscope signal rate of rotation (w) multiplied by the length of displacement from the wrist joint to the center of the conformal wearable and wireless inertial sensor system (len) as shown in Equation 1. An alternative means of calculating the derived velocity can be achieve by integrating the acceleration signal as shown in Equation 2.

$$\text{Tremor Power} = m^*(a-g)^*(w^*len) \qquad \text{Equation 1:}$$

$$\text{Tremor Power} = m^*(a-g)^*((\text{integral from (time 1) to (time 2))} \text{ of } (\text{acceleration(time)})^*dt)) \text{ such that (time 1) and (time 2) establish the temporal bounds to derive velocity} \qquad \text{Equation 2:}$$

Alternate embodiments for ascertaining and calculating tremor power may be applied as a function of relevant and/or predetermined aspects of the subject's anthropometric mass properties and subject's anthropometric length properties and inertial signal data that quantifies the tremor response as shown in Equation 3.

$$\text{Tremor Power} = f(\text{subject's anthropometric mass properties and subject's anthropometric length properties, inertial signal data that quantifies the subject's tremor response}) \qquad \text{Equation 3:}$$

Alternate embodiments for ascertaining and calculating tremor power may be applied as a function of relevant and/or predetermined aspects of the DBS system's quantified feedback response, such as from a conformal wearable and wireless inertial sensor.

The deep brain stimulation amplitude-derived power (DBS power) can be determined effectively as a function of Ohm's Law, which can incorporate the deep brain stimulation amplitude current (I) and the effective resistance (impedance) of the deep brain stimulation system (R), as shown in Equation 4.

$$\text{DBS Power} = (I^2)^*R \qquad \text{Equation 4:}$$

Alternate embodiments for ascertaining and calculating DBS Power may be applied as a function of relevant and/or predetermined aspects of the DBS system's parameter configuration as shown in Equation 5.

$$\text{DBS Power} = f(\text{amplitude, stimulation frequency, pulse width, polarity}) \qquad \text{Equation 5:}$$

Tremor power and DBS power are contrarian with respect to each other. For example, maximal DBS power would result in minimal tremor power. However, this scenario would inflict the most rapid depletion of the deep brain stimulation system battery, which could require the need for the surgical implantation of a new battery. By contrast, minimal DBS power would result in maximal tremor power, which would negate the deep brain stimulation system's efficacy. The dependent variable enabling optimal power is the effective power, which represents the minimization of the tremor power in conjunction with DBS power as provided in Equation 6.

$$\text{Effective Power} = ((\text{SquareRoot}(\text{Tremor Power}))^* (\text{SquareRoot}(\text{DBS Power}))) \qquad \text{Equation 6:}$$

Figure 10:
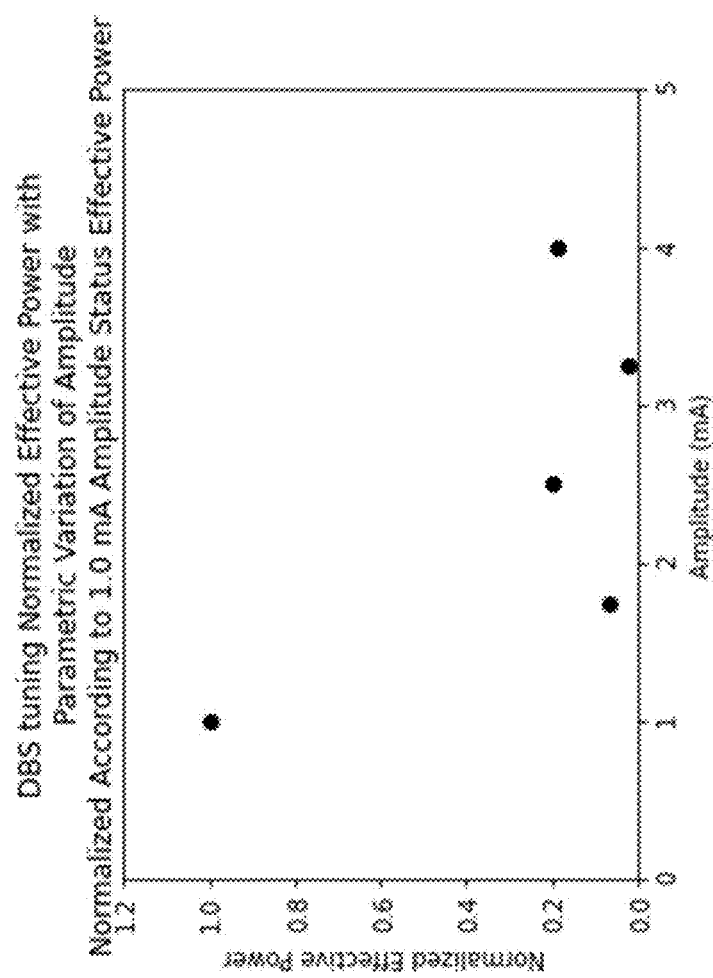
FIG. 10 shows a representative demonstration for the acquisition of optimal power derived from the effective power for five deep brain stimulation amplitude settings (1.0 mA, 1.75 mA, 2.5 mA, 3.25 mA, and 4.0 mA) that are normalized according to the effective power corresponding to the 1.0 mA amplitude setting, with respect to a subject with Parkinson's disease.

FIG. 10 demonstrates the optimal power for a subject with Parkinson's disease treated by deep brain stimulation, which are derived from the averaging of the effective power for five deep brain stimulation amplitude settings (1.0 mA, 1.75 mA, 2.5 mA, 3.25 mA, and 4.0 mA). Note the amplitude corresponding with the optimal power corresponding to 3.25 mA is achieved within the constraining bounds of the deep brain stimulation amplitude settings.

The discretion of the clinician overseeing the optimization of the deep brain stimulation amplitude setting could modify the exponentials for tremor power and DBS power per the modification of the optimal power dependent variable as shown in Equation 7.

$$\text{Effective Power} = (((\text{Tremor Power})\hat{\ }x)*((\text{DBS Power})\hat{\ }y))), \text{ where, } x+y=1 \quad \text{Equation 7:}$$

This modified tremor power would enable the clinician to further adapt the multidisciplinary design optimization of the deep brain stimulation system amplitude parameter configuration setting to accommodate the patient lifestyle scenario. For example, a young subject presumed to be robust to additional deep brain stimulation battery surgery implantation could have (x=0.75) and (y=0.25) for maximal tremor suppression quality of life. By comparison, an elderly subject with paramount risk to additional deep brain stimulation battery surgery implantation could have (x=0.25) and (y=0.75) in order to mitigate the risk of an additional surgery for the implantation of a new deep brain stimulation battery.

In some embodiments, an orientation filter can be implemented in conjunction with the inertial sensor system. An orientation filter enables the inertial sensor signal data to resolve spatial orientation of displacement, velocity, and acceleration as a function of time. For example, orientation filters applied with inertial sensor signal data provide aerospace systems with guidance, navigation, and control. The derivation of displacement, velocity, and acceleration as a function of time from the orientation filter based on inertial sensor signal data would advance the acuity of deriving the tremor power for the optimization of the deep brain stimulation parameter configurations. A suitable orientation filter would be a Kalman filter.

In some embodiments, the multidisciplinary design optimization of multiple parameter configuration variables for achieving further advances with multidisciplinary design optimization of deep brain stimulation parameter configurations can be used. The tremor power would still be derived as defined above. However, the DBS power would be a function of amplitude, stimulation frequency, pulse width, and polarity.

The establishment of the multidisciplinary design optimization design space could be derived by incremental modification of the respective parameter configurations for deep brain stimulation, gradient response to the change in modified optimal power, or a multitude of available numerical methods feasible for multidisciplinary design optimization. The independent variables, such as amplitude, stimulation frequency, pulse width, and polarity, could be constrained as the discretion of the supervising clinical resources for patient safety.

Best modes of practice can incorporate cloud and/or fog computing architectures. Cloud computing architectures involve transmission of the sensor system data (e.g., conformal wearable and wireless inertial sensors) to a cloud computing resource for post-processing of the signal data and derivation of the multidisciplinary design optimization with subsequent transmission of the recommended parameter configuration for the deep brain stimulation system. Fog computing architecture involves a portion of the post-processing of the signal data and derivation of the multidisciplinary design optimization at the wearable system level based on availability of computational resources with computationally intensive aspects of the multidisciplinary design optimization of the deep brain stimulation system parameter configuration assigned to the cloud computing resources.

Multidisciplinary Design Optimization Phase (Pseudo Code)

In order to realize multidisciplinary design optimization for a neuromodulation system, the design space of the dependent variable based on the input of the independent variable should be defined. A representative embodiment of multidisciplinary design optimization for a neuromodulation system is provided for deep brain stimulation for Parkinson's disease with wearable inertial sensors providing feedback. The representative pseudo code (i.e., the verbalization of the software program's functionality, which facilitates a skilled programmer to achieve the desired effects of the proposed algorithm) for the design space of the dependent variable based on the input of the independent variable is provided in a sequential manner below. For other versions of neuromodulation, such as transcranial Direct Current Stimulation (tDCS), representative embodiments of the pseudo code can be readily derived by one skilled in the art, while incorporating a quantified feedback of the response to the neuromodulation intervention.

General Pseudo Code:
1. Define amplitude (input current) for deep brain stimulation, deep brain stimulation electrode impedance (resistance), anthropometric hand mass, and gravitational acceleration.
2. Upload quantified wearable inertial sensor signal data defining tremor response to prescribed deep brain stimulation parameter configuration from step 1.
3. Acquire inertial signal data (accelerometer or accelerometer and gyroscope) and post-process accelerometer signal to derive acceleration magnitude, hereinafter referred to as post-processed inertial signal data.
4. Parse post-processed inertial signal data into equivalent time intervals, such as two second intervals of the post-processed inertial signal data.
5. Visualize post-processed inertial signal data by plotting a graph.
6. Within each time interval ascertain the maximal acceleration and corresponding velocity (velocity corresponding with maximal acceleration, which are derived from the post-processed inertial signal data).
7. Continue step 6 for each post-processed inertial signal data time interval.
8. Derive tremor power for each time interval as a function of hand mass, tremor acceleration (maximal acceleration less gravitation acceleration), and corresponding velocity (e.g., using any of Equations 1-3).
9. Derive mean tremor power in accordance with the total number of time interval sequences for the respective post-processed inertial signal data.
10. Derive DBS power as a function of amplitude (input current) for deep brain stimulation and deep brain stimulation electrode impedance (resistance) (e.g., using any of Equations 4-5).
11. Derive effective power as a function of the square root of tremor power multiplied by square root of DBS power (see, e.g., Equation 6).
12. Repeat steps 1 through 11 for the series of equally incremented deep brain stimulation amplitude settings with other parameter configuration settings held constant.
13. Derive normalized effective power based on the effective power with the greatest magnitude.
14. Visualize the normalized effective power as a function of amplitude (input current) for deep brain stimulation, such as illustrated in FIG. 10.
15. Select the amplitude (input current) for deep brain stimulation corresponding with the minimal normalized effective power. The selected amplitude (input current) for deep brain stimulation with the other parameter configuration settings held constant constitutes the optimal parameter configuration for deep brain stimulation.

Modification to General Pseudo Code (Reducing Series of Amplitude Increments)

Another embodiment of the general pseudo code can reduce the series of amplitude increments by determining the change in slope with respect to the normalized effective power and amplitude for deep brain stimulation. For incrementally increased amplitude for deep brain stimulation (low to high) a local minimal normalized effective power would be ascertained by a negative slope (normalized effective power per amplitude) with subsequent transition to a positive slope (normalized effective power per amplitude). For incrementally decreased amplitude for deep brain stimulation (high to low) a local minimal normalized effective power would be ascertained by a positive slope (normalized effective power per amplitude) with subsequent transition to a negative slope (normalized effective power per amplitude). The incrementally increased or incrementally decreased amplitude increments could terminate upon the normalized effective power exceeding or passing a threshold for a prescribed minimal. The threshold can be prescribed by those conducting the optimization endeavor, such as a supervising clinical team.

Another embodiment envisions that upon the discovery of a local and/or global minimal a bound respective of the amplitude for deep brain stimulation corresponding to the local and/or global minimal normalized effective power can be defined. A series of smaller increments of amplitude for deep brain stimulation can be applied and the 'General pseudo code' and/or 'Modification to general pseudo code (reducing series of amplitude increments)' can achieve a more optimal global minimal normalized effective power with the corresponding amplitude (input current) for deep brain stimulation with the other parameter configuration settings held constant constituting the optimal parameter configuration for deep brain stimulation. The series of smaller increments enables the ability to ascertain a more precise local and/or global minimal normalized effective power.

Another embodiment envisions the expansion of the number of independent variables to define DBS Power from one independent (amplitude) to all variables the define the neuromodulation parameter configuration, such as for deep brain stimulation: amplitude, stimulation frequency, pulse width, and polarity, which is prescribed by the DBS Power (four independent variables) function shown in Equation 8.

DBS Power (four independent variables)=Function (amplitude, stimulation frequency, pulse width, polarity)   Equation 8:

DBS Power (four independent variables) could be applied as a modification to the DBS Power function for the acquisition of a minimal power for the effective power. The 'General pseudo code' and/or 'Modification to general pseudo code (reducing series of amplitude increments)' defined above could be applied in accordance to the four independent variables by achieving optimal independent variables in ascending order of clinically prescribed priority, descending order of clinically prescribed priority, or an order of the clinically prescribed preference.

Additionally, any numerical optimizer capable of converging upon a minimum dependent variable for a neuromodulation system, such as effective power for deep brain stimulation, can achieve an optimal parameter configuration for the neuromodulation system, such as amplitude, stimulation frequency, pulse width, and polarity for deep brain stimulation.

An additional embodiment considers the alternative of applying interpolation through regression, such as an interpolation spline to achieve a more precise optimal (minimal dependent variable) based on the regression relationships, such as a spline, for the acquisition of a more precise independent variable or set of independent variables (parameter configuration).

EXAMPLES

Figure 1:
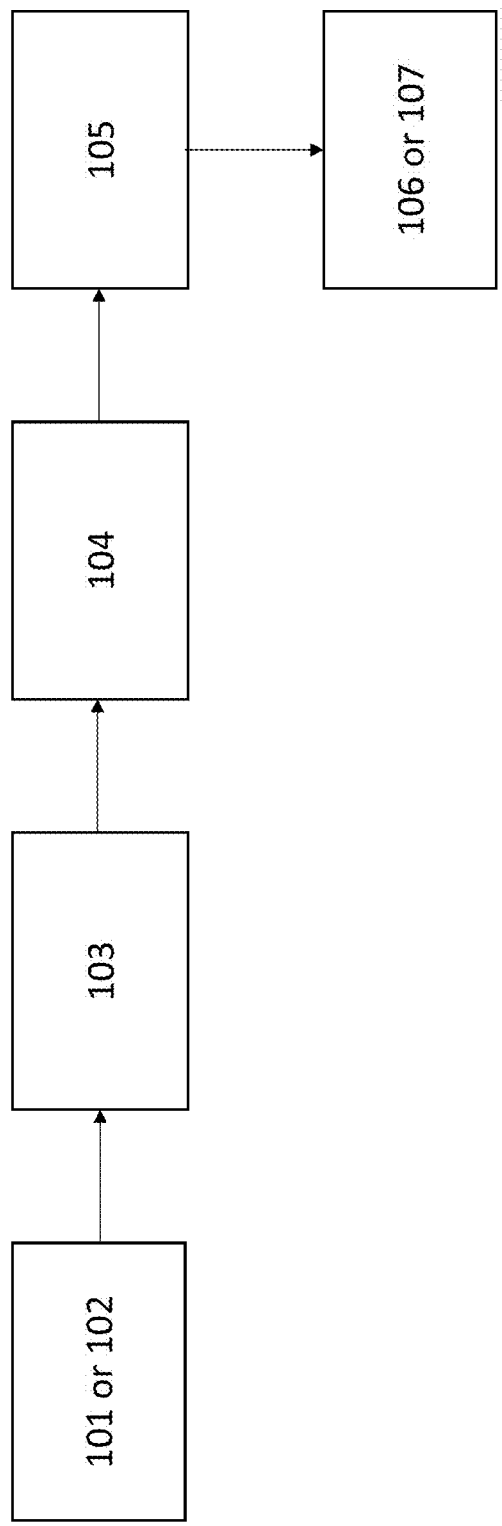
FIG. 1 shows a flow diagram for a multidisciplinary design optimization process for a launch vehicle.

FIG. 1 shows a flow diagram for an example of a multidisciplinary design optimization process for a launch vehicle. Multidisciplinary design optimization for a launch vehicle can be exemplified by the application of an independent variable 101 or series of independent variables 102 (e.g., Stage 1 specific impulse; Stage 2 specific impulse; Initial mass; Initial acceleration; Number of rocket engines per stage 1; Number of rocket engines per stage 2) processed to a design space 103, which is defined by a complex series of performance estimation relationships and cost estimating relationships, that is processed by an optimization algorithm 104 that is suitable for achieving multidisciplinary design optimization, which yields an optimal dependent variable 105 that corresponds to an optimal independent variable 106 or series optimal of independent variables 107.

Figure 2:
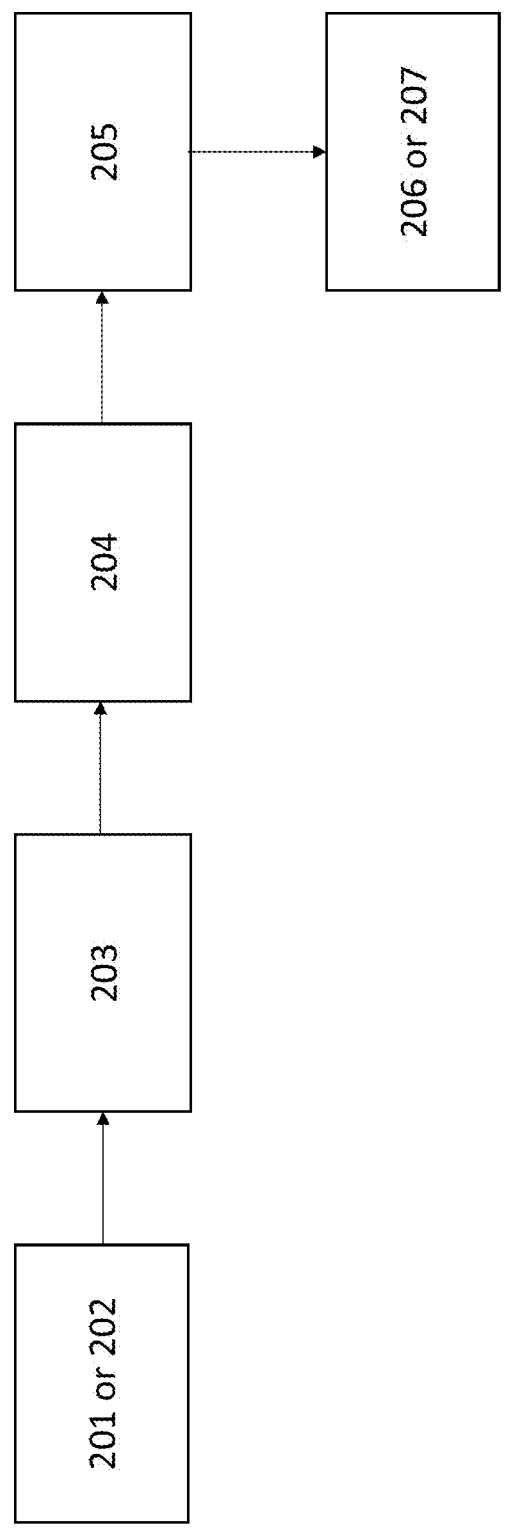
FIG. 2 shows a flow diagram for a multidisciplinary design optimization of a neuromodulation system.

FIG. 2 shows a flow diagram for a multidisciplinary design optimization of a neuromodulation system. The multidisciplinary design optimization of neuromodulation system can be exemplified by the application of independent variable 201 (such as amplitude, frequency, pulse width, or polarity) or series of independent variables 202 (such as amplitude, stimulation frequency, pulse width, and polarity, or any combination thereof) processed to a design space 203, which is design space defining the dependent variable that can be defined as the quantified response, such as from a wearable inertial sensor system, resultant of therapeutic intervention provided by a neuromodulation system, such as deep brain stimulation to the brain of the subject being treated (or other forms of neural stimulation), that is processed by an optimization algorithm 204 that is suitable for achieving multidisciplinary design optimization, which yields an optimal dependent variable 205 that corresponds to an optimal independent variable 206 (such as amplitude) or optimal series of independent variables 207 (such as amplitude, stimulation frequency, pulse width, and polarity, or any combination thereof).

Figure 3:
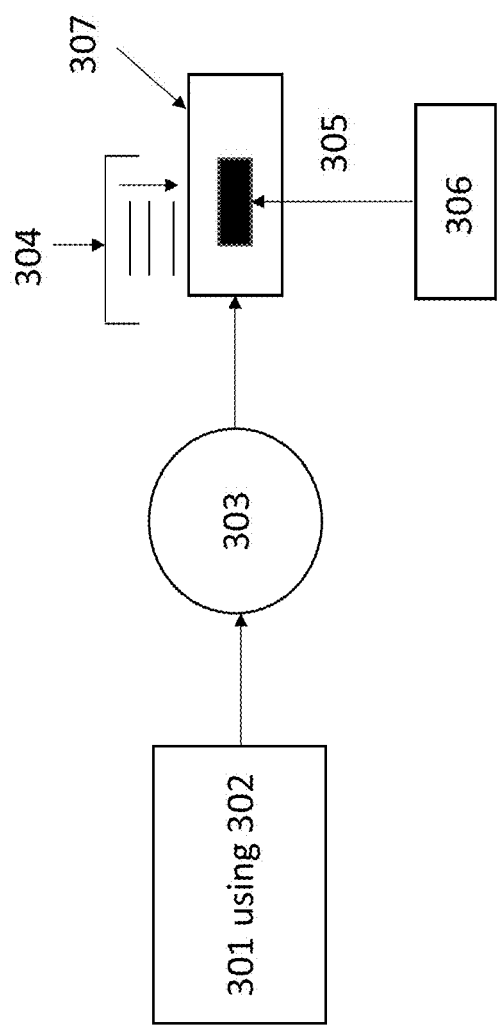
FIG. 3 shows a flow diagram for a neuromodulation system, such as deep brain stimulation, with quantified feedback (response) from a wearable system.

FIG. 3 shows a schematic of a neuromodulation system, such as deep brain stimulation system with quantified feedback (response) from a wearable system. The neuromodulation system 301 with a prescribed parameter configuration 302 (such as amplitude, stimulation frequency, pulse width, and/or polarity) provides the subject's brain 303 with therapeutic intervention that modifies (e.g., suppresses) the subject's tremor 304 based on quantified feedback (response) 305 using a wearable system 306 (such as a wearable inertial sensor system) mounted to a predetermined aspect of the subject's body 307 (such as the dorsum of the hand).

Figure 4:
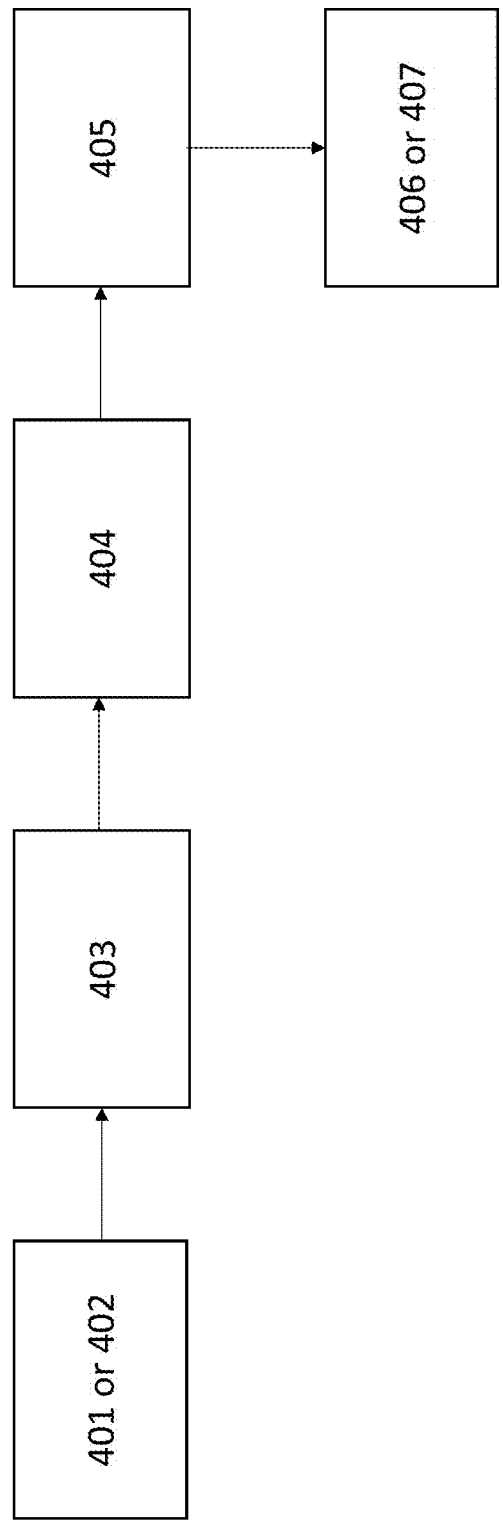
FIG. 4 shows a flow diagram for a multidisciplinary design optimization of a neuromodulation system, such as deep brain stimulation for treatment of movement disorder, such as Parkinson's disease.

FIG. 4 shows a flow diagram for an embodiment of the multidisciplinary design optimization of Neuromodulation system, such as deep brain stimulation for treatment of movement disorder, such as Parkinson's disease. Multidisciplinary design optimization of a neuromodulation system, such as deep brain stimulation for treatment of movement disorder, such as Parkinson's disease, can be exemplified by the application of an independent variable 401 (such as amplitude, frequency, pulse width, or polarity) or series of independent variables 402 (that are simultaneously applied) (such as amplitude, stimulation frequency, pulse width, and polarity, or any combination thereof) processed to a design space 403, which is design space defining the dependent variable that can be defined as the quantified response resultant of therapeutic intervention provided by the neuromodulation system, such as deep brain stimulation for treatment of movement disorder, such as Parkinson's disease, to the brain of the subject being treated, that is processed by a optimization algorithm 404 that is suitable for achieving multidisciplinary design optimization, which yields an optimal dependent variable 405 that corresponds to an optimal independent variable 406 (such as amplitude, frequency, pulse width, or polarity) or optimal series of independent variables 407 (such as amplitude, stimulation frequency, pulse width, and polarity, or any combination thereof).

FIG. 5 shows an example of a conformal wearable and wireless inertial sensor system mounted about the dorsum of the hand. The conformal wearable and wireless inertial sensor system 501 is mounted about the dorsum of the hand 502, which best quantifies the response to a movement disorder therapeutic intervention, such as deep brain stimulation.

FIGS. 6a to 6e show graphs of an accelerometer signal based on the acceleration magnitude for a subject with Parkinson's disease hand tremor recorded by a conformal wearable and wireless inertial sensor system. FIG. 6a shows the acceleration signal of a subject with Parkinson's disease hand tremor with deep brain stimulation set to amplitude 1.0 mA status. FIG. 6b shows the acceleration signal of a subject with Parkinson's disease hand tremor with deep brain stimulation set to amplitude 1.75 mA. FIG. 6c shows the acceleration signal of a subject with Parkinson's disease hand tremor with deep brain stimulation set to amplitude 2.5 mA. FIG. 6d shows the acceleration signal of a subject with Parkinson's disease hand tremor with deep brain stimulation set to amplitude 3.25 mA. FIG. 6e shows the acceleration signal of a subject with Parkinson's disease hand tremor with deep brain stimulation set to amplitude 4.0 mA.

Figure 7:
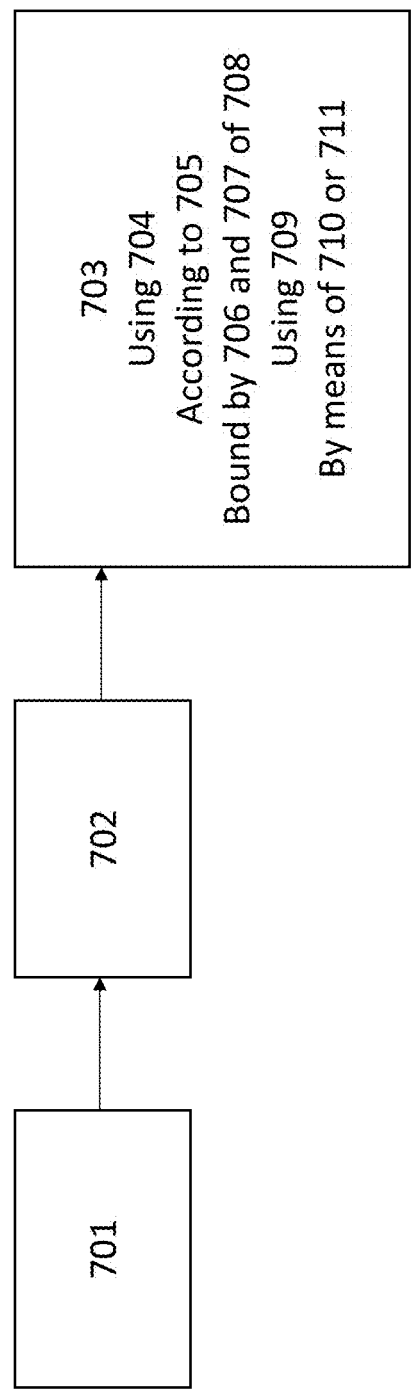
FIG. 7 shows a representation of a process for acquisition of signal data.

FIG. 7 shows a flow diagram representation of the process for the acquisition of signal data in incremental methodology with future embodiment for time stepping for real time applications, comprising securing the conformal wearable to dorsum of the hand 701; wirelessly activating the conformal wearable for acquiring the inertial sensor signal data with subsequent transmission of the wireless signal data to a cloud computing resource for storage 702; and protocol sequence 703 modifying the deep brain stimulation clinical programmer 704 to the following parameter configuration scenarios 705 with prescribed upper bound 706 and lower bound 707 of a predetermined independent variable (such as amplitude, frequency, pulse width, or polarity) 708 and predetermined number of increments 709 that can be manually (clinically) modified 710 or incremented in a real time increment 711. In alternative embodiments, the wearable can be placed on a more representative aspect of the human anatomy, with respect to the neuromodulation response.

Figure 8B:
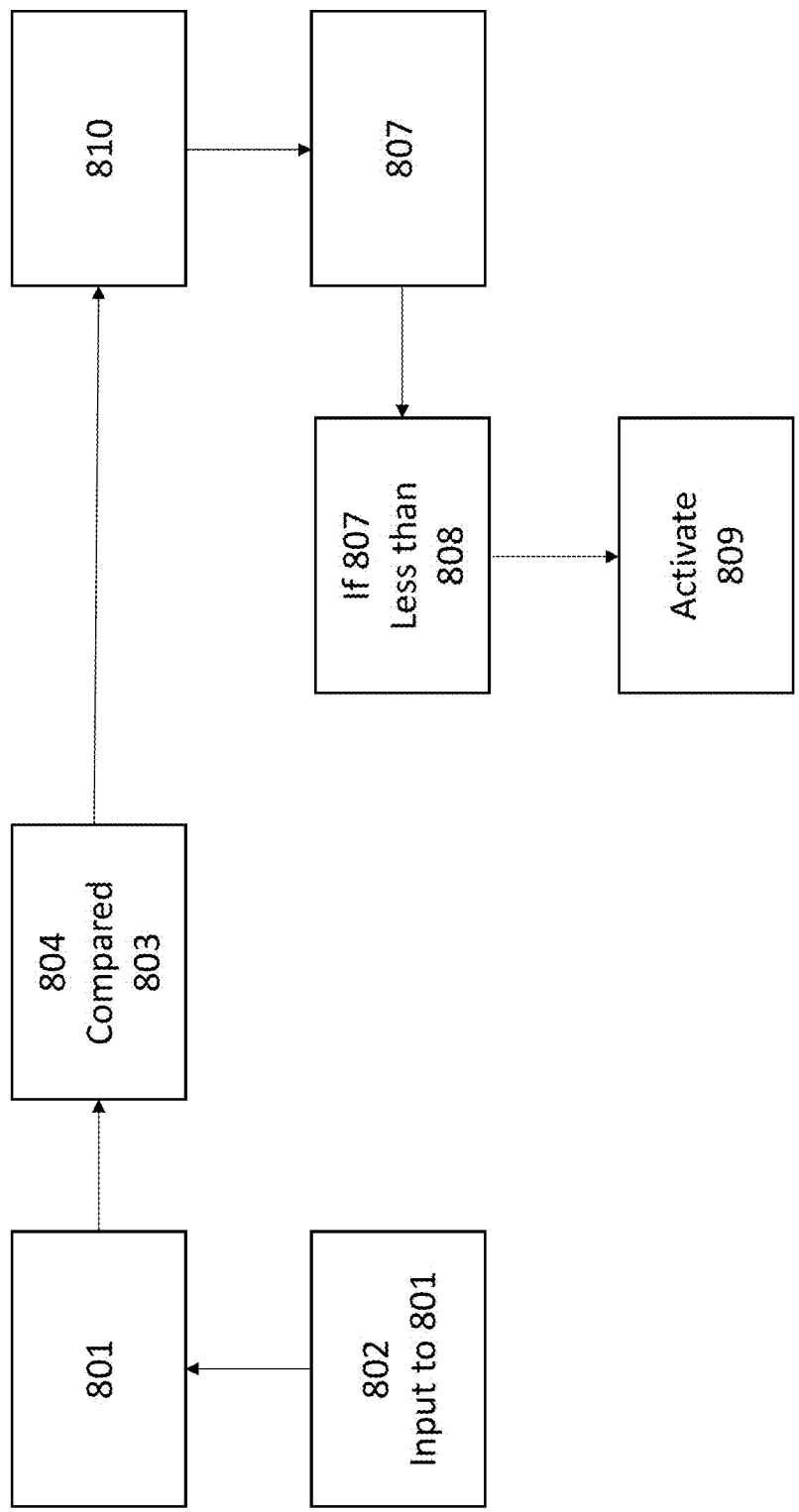

FIGS. 8a and 8b show representations of the process for machine learning classification. FIG. 8a shows for a subject, such as a person with movement disorder being treated a by neuromodulation system 801 with a previously (historically) optimized parameter configuration 802, previously (historically) quantified feedback signal data 803 (such as inertial signal data) compared to a current (present time) quantified feedback signal data 804 (such as inertial signal data). Previously (historically) quantified feedback signal data 803 (such as inertial signal data) and current (present time) quantified feedback signal data 804 (such as inertial signal data) are post-processed to a clinically relevant feature set. The clinically relevant feature set 805 is applied to a machine learning algorithm 806 to derive a classification accuracy 807 that differentiates between the previously (historically) quantified feedback signal data 803 (such as inertial signal data) and current (present time) quantified feedback signal data 804 (such as inertial signal data). If the classification accuracy 807 falls below a prescribed threshold 808, the multidisciplinary design optimization process 809 for the neuromodulation system could then be initiated.

FIG. 8(b) shows alternative embodiments that are inclusive of artificial intelligent algorithms capable of providing classification accuracy with respect to the quantified wearable signal data response to a neuromodulation parameter configuration, such as a deep learning algorithm. For a subject, such as a person with movement disorder being treated a by neuromodulation system 801 with a previously (historically) optimized parameter configuration 802, previously (historically) quantified feedback signal data 803 (such as inertial signal data) is compared to a current (present time) quantified feedback signal data 804 (such as inertial signal data). Previously (historically) quantified feedback signal data 803 (such as inertial signal data) and current (present time) quantified feedback signal data 804 (such as inertial signal data) is applied to a deep learning algorithm 810 to derive a classification accuracy 807 that differentiates between the previously (historically) quantified feedback signal data 803 (such as inertial signal data) and current (present time) quantified feedback signal data 804 (such as inertial signal data). If the classification accuracy 807 falls below a prescribed threshold 808, the multidisciplinary design optimization process 809 for the neuromodulation system 801 could then be initiated.

Another alternative embodiment would be for the continuous operation of the MDO neuromodulation process, or the activation of the MDO neuromodulation process in accordance with a time incremented manner.

Figure 9A:
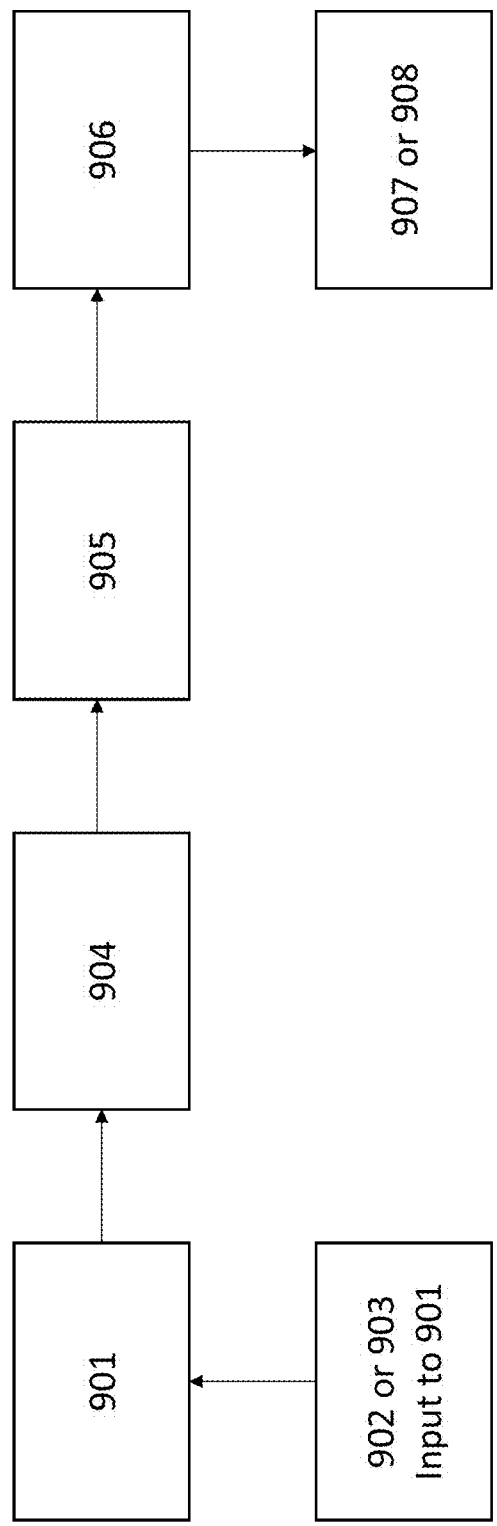
FIGS. 9a and 9b show representations of a process for a design optimization phase, e.g., a pathway for closed-loop optimization.
Figure 9B:
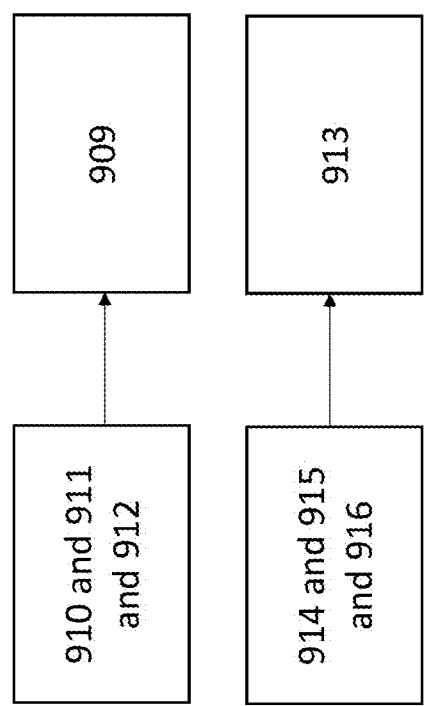

FIGS. 9a and 9b shows a representation of a process for a multidisciplinary design optimization phase (a pathway for closed-loop optimization). In FIG. 9a a multidisciplinary design optimization of neuromodulation system, such as deep brain stimulation for treatment of movement disorder, such as Parkinson's disease, can be exemplified by the application of an independent variable 902 (such as amplitude, frequency, pulse width, or polarity) or series of independent variables 903 (such as amplitude, stimulation frequency, pulse width, and polarity, or any combination thereof) processed to a design space 904, which is design space defining the dependent variable that can be defined as the quantified response resultant of therapeutic intervention provided by a neuromodulation system, such as deep brain stimulation for treatment of movement disorder, such as Parkinson's disease, to the brain of the subject being treated, that is processed by an optimization algorithm 905 that is suitable for achieving multidisciplinary design optimization, which yields an optimal dependent variable 906 (e.g., effective power) that corresponds to an optimal independent variable 907 (such as amplitude, frequency, pulse width, or polarity) or series of independent variables 908 (such as amplitude, stimulation frequency, pulse width, and polarity, or any combination thereof).

FIG. 9b shows tremor power 909 is derived as a function of a subject's anthropometric mass properties 910 and a subject's anthropometric length properties 911 and inertial signal data that quantifies the tremor response 912. DBS power 913 is derived as a function of deep brain stimulation amplitude current 914 and of the deep brain stimulation system effective resistance 915 (impedance). In some embodiments, ascertaining and calculating DBS Power 913 may be applied as a function of relevant and/or predetermined aspects of the DBS system's parameter configuration 916 inclusive of amplitude, stimulation frequency, pulse width, and polarity.

Figure 9C:
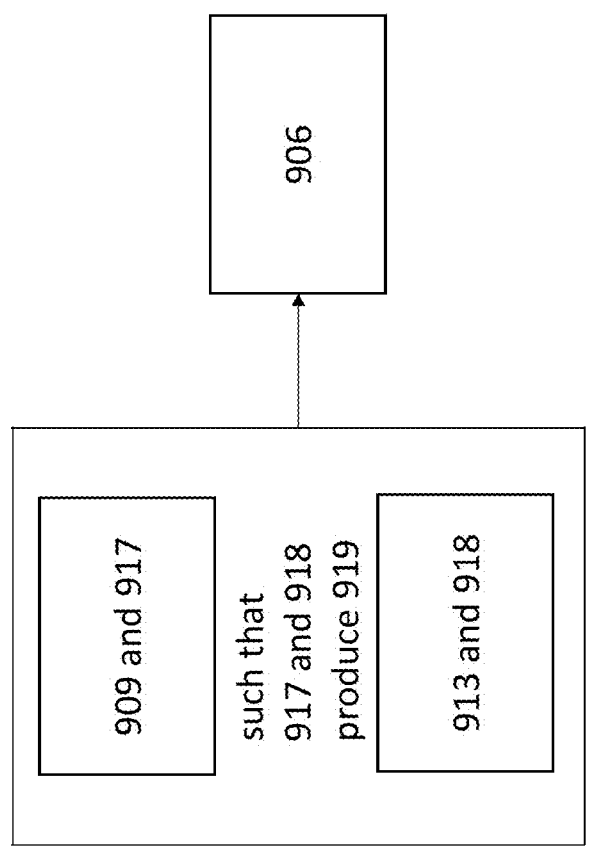
FIG. 9c shows a representation of how effective power can be calculated.

FIG. 9c shows effective power 906 is the combined multiplication of tremor power 909 and DBS power 913, such that tremor power 909 is raised to exponent x 917 and DBS power 913 is raised to exponent y 918 under the constraint that the sum of exponent x 917 and exponent y 918 equals unity 919, i.e., (exponent x)+(exponent y)=1.

FIG. 10 is a representative graph demonstrating the acquisition of optimal power derived from the effective power for five deep brain stimulation amplitude settings (1.0 mA, 1.75 mA, 2.5 mA, 3.25 mA, and 4.0 mA) that are normalized according to the effective power corresponding to the 1.0 mA amplitude setting, with respect to a subject with Parkinson's disease. The patient was a mid-60's year old [female] with Parkinson's disease. Electrodes were implanted to provide deep brain stimulation of the bilateral subthalamic nucleus region of the brain and connected to an implantable pulse generator for deep brain stimulation. A wearable inertial sensor was attached to the dorsum of the hand of the patient to measure the inertial signal. The inertial signal acquired by the conformal wearable inertial sensor was transmitted to a computer system for post-processing of the inertial signal, such as for multidisciplinary design optimization process. In this example, the parameter configurations were set as follows: stimulation frequency, pulse width, and polarity were held constant to their original clinically prescribed settings. The deep brain stimulation amplitude parameter was set to 1.0 mA, 1.75 mA, 2.5 mA, 3.25 mA, and 4.0 mA. Deep brain stimulation power was computed based on the relationship to the deep brain stimulation amplitude parameter settings. Tremor power was computed as a relationship of the inertial signal data. Effective power was computed based on the relationship to the deep brain stimulation power and tremor power. FIG. 10 shows the resultant plot normalized to the effective power at 1.0 mA. Based on this example, 3.25 mA appears to have produced the optimal performance based on the prescribed deep brain stimulation amplitude parameters, for which with regards to this scenario the deep brain stimulation amplitude parameter constitutes the representative independent variable. This process can be applied to other parameter configurations for the other independent variables. This process can be repeated to fine tune the optimal amplitude, or the process can be repeated with the amplitude fixed and varying the other remaining independent variables.

As such, the optimization process incorporates the wearable and wireless inertial sensor system for quantifying the tremor response through inertial signal data based on the respective deep brain stimulation parameter configurations, which is a representative example for quantifying the feedback response of a neuromodulation parameter configuration. Normalized effective power as a function of amplitude visualizes the global optimal for effective power.

Figure 11A:
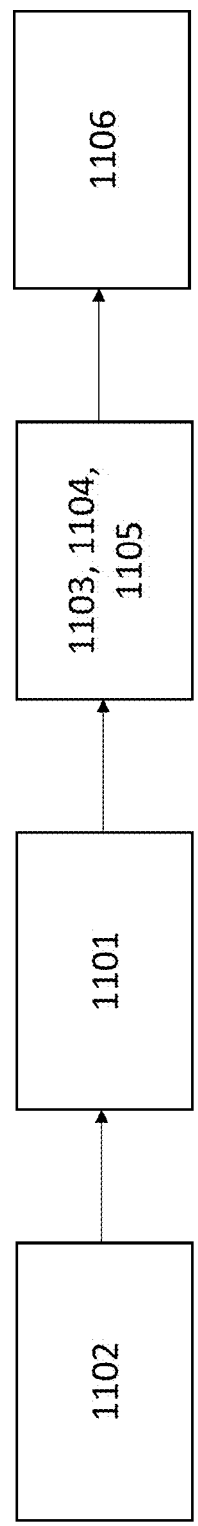
FIGS. 11a-11d show representations of a process for other embodiments of a design optimization phase, e.g. a pathway for closed-loop optimization.

FIGS. 11a-11d show representations of another process for a multidisciplinary design optimization phase (a pathway for closed-loop optimization). FIG. 11a shows that the spatial acuity of the tremor response to deep brain stimulation parameter configurations can be augmented through the application of an orientation filter 1101 (such as a Kalman filter). Using the inertial signal data that quantifies the tremor response 1102 (previously defined in FIGS. 9a,b,c; Inertial signal data quantifying tremor response is inherent to deriving effective power) an orientation filter 1101 (such as a Kalman filter) can ascertain advanced spatial representation of displacement 1103, velocity 1104, and acceleration 1105 to determine more high fidelity computation of tremor power 1106 (previously defined in FIGS. 9a,b,c; Tremor power is inherent to deriving effective power).

Figure 11B:
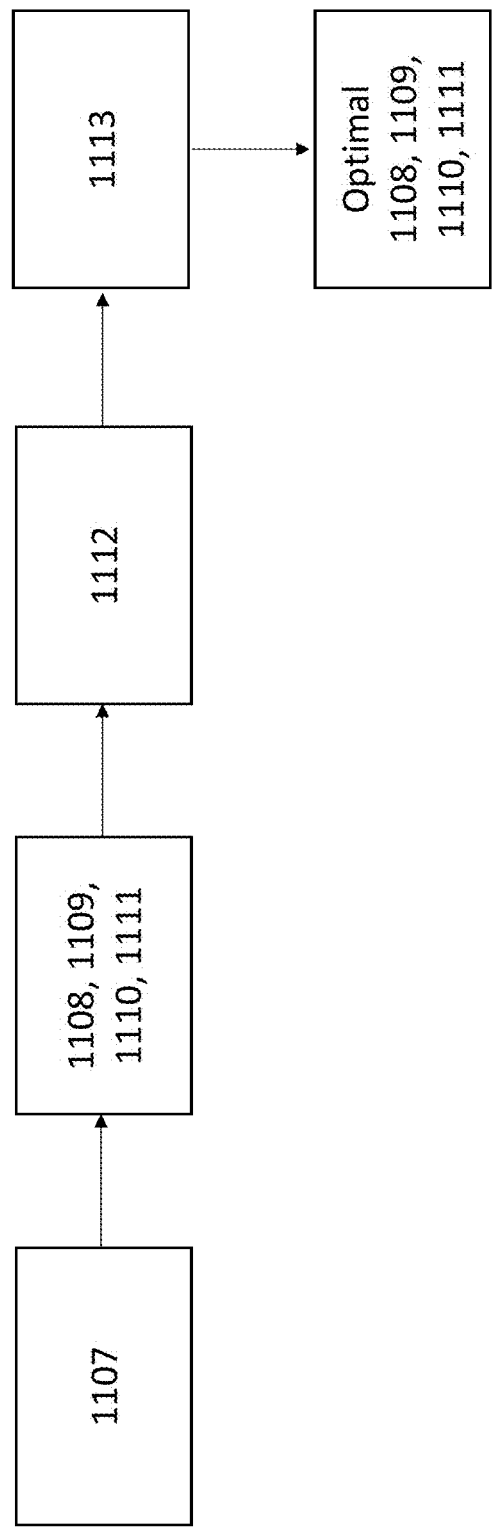

FIG. 11b shows a flow diagram of how to sequentially optimize the parameter configurations one parameter at a time. Multidisciplinary design optimization of parameter configurations can be implemented by a single parameter, such as amplitude, the applications of all available parameters (e.g., amplitude, stimulation frequency, pulse width, and polarity), or the application of any combination of available parameters (e.g., amplitude, stimulation frequency, pulse width, polarity, or any combination thereof) simultaneously applied as illustrated in FIG. 4. An alternative embodiment would be to sequentially optimize the parameter configurations 1107 one parameter at a time, such as first amplitude 1108, then stimulation frequency 1109, then pulse width 1110, and finally polarity 1111 through the application of an optimization algorithm 1112 that is suitable for achieving multidisciplinary design optimization, which yields an optimal dependent variable 1113 per each optimized independent variable parameter (amplitude 1108, stimulation frequency 1109, pulse width 1110, and polarity 1111). The sequential organization can be prescribed based on the discretion of the supervising clinician so that any one of the available parameters 1107 is optimized first. Then the optimization process is repeated so that any remaining parameter 1107 is optimized second, and so on until all parameters have been optimized in a desired order.

Figure 11C:
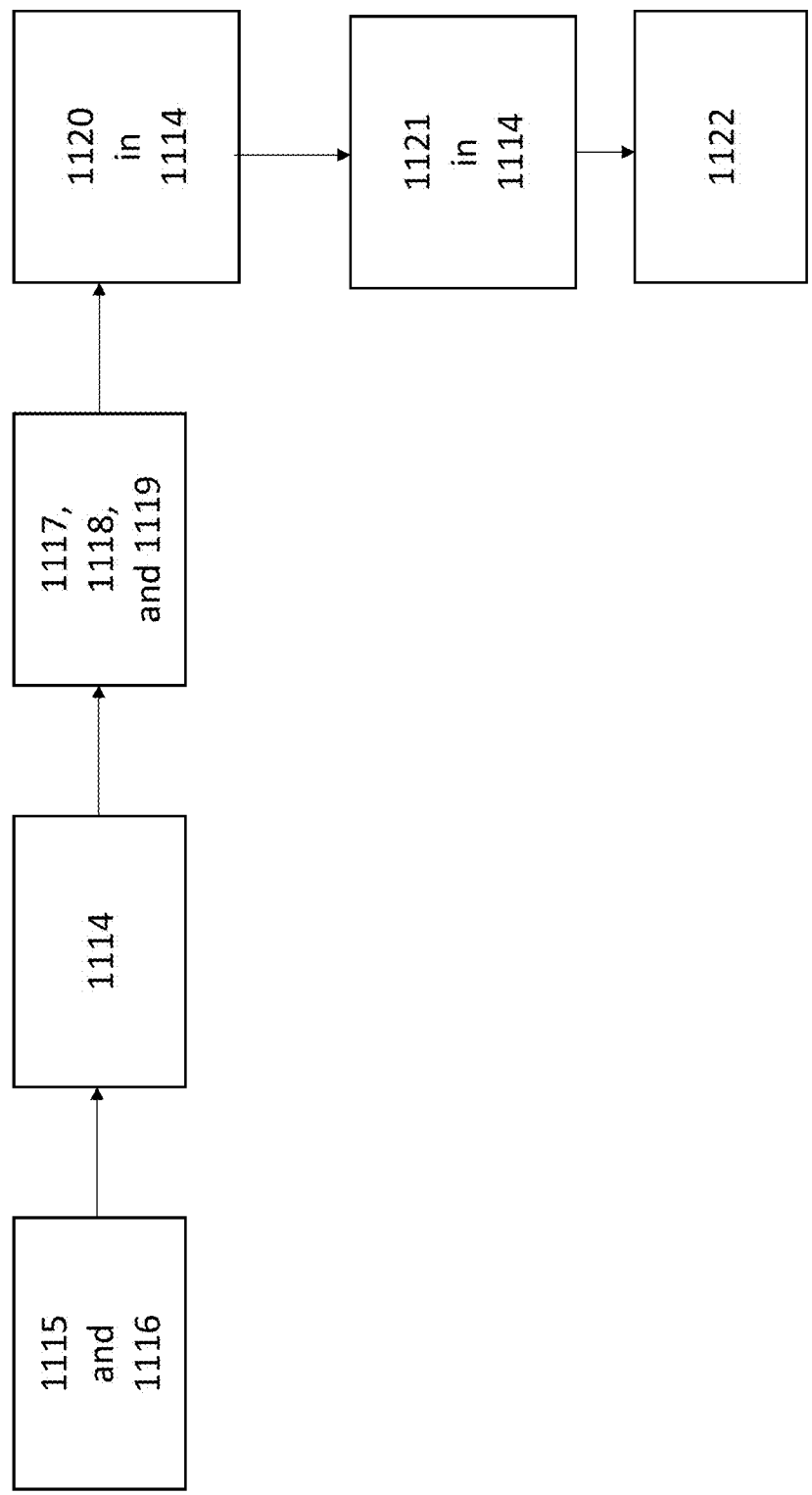

Alternative embodiments can apply cloud computing architecture 1114 as shown in FIG. 11c. Cloud computing architecture 1114 involves inertial signal data that quantifies the tremor response 1115 (previously defined in FIG. 9) and parameter configuration 1116 up to the cloud computing architecture 1114 for computation of the tremor power 1117, DBS power 1118, and effective power 1119. Using the optimization algorithm 1120 at the cloud computing architecture 1114 that is suitable for achieving multidisciplinary design optimization, the optimal parameter configuration 1121 is transmitted from the cloud computing architecture 1114 to the subject undergoing deep brain stimulation 1122.

Figure 11D:
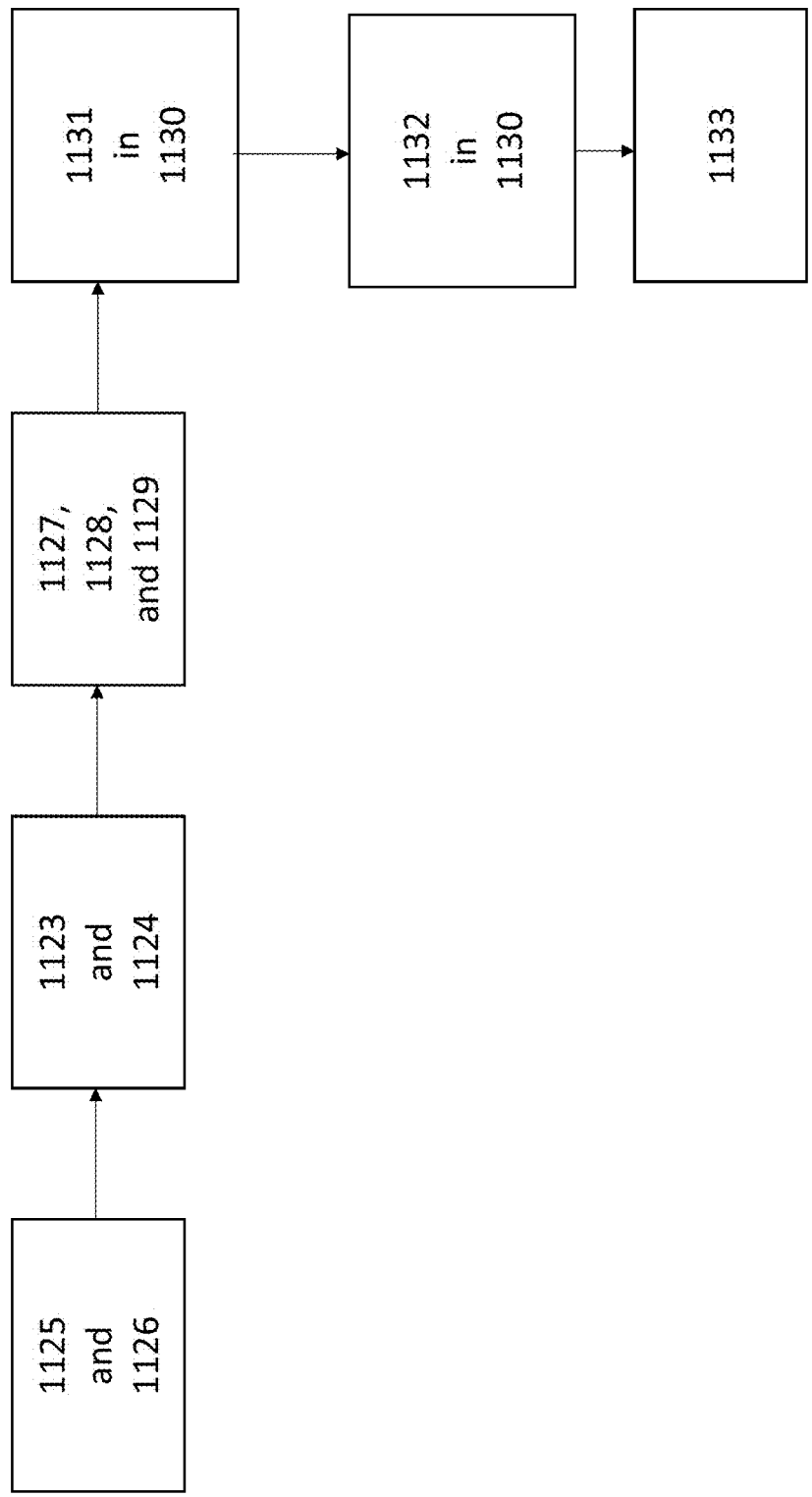

Alternative embodiments can apply Fog computing architecture 1123 as shown in FIG. 11d. Fog computing architecture proximal to sensor level 1124 computes inertial signal data that quantifies the tremor response 1125 (previously defined in FIG. 9) and parameter configuration 1126 to derive the tremor power 1127, DBS power 1128, and effective power 1129, which is conveyed to Fog computing architecture proximal to Cloud level 1130. Using the optimization algorithm 1131 that is suitable for achieving multidisciplinary design optimization at the Fog computing architecture proximal to cloud level 1130, the optimal parameter configuration 1132 is transmitted from the fog computing architecture proximal to cloud level 1130 to the subject undergoing deep brain stimulation 1133.

Figure 12:
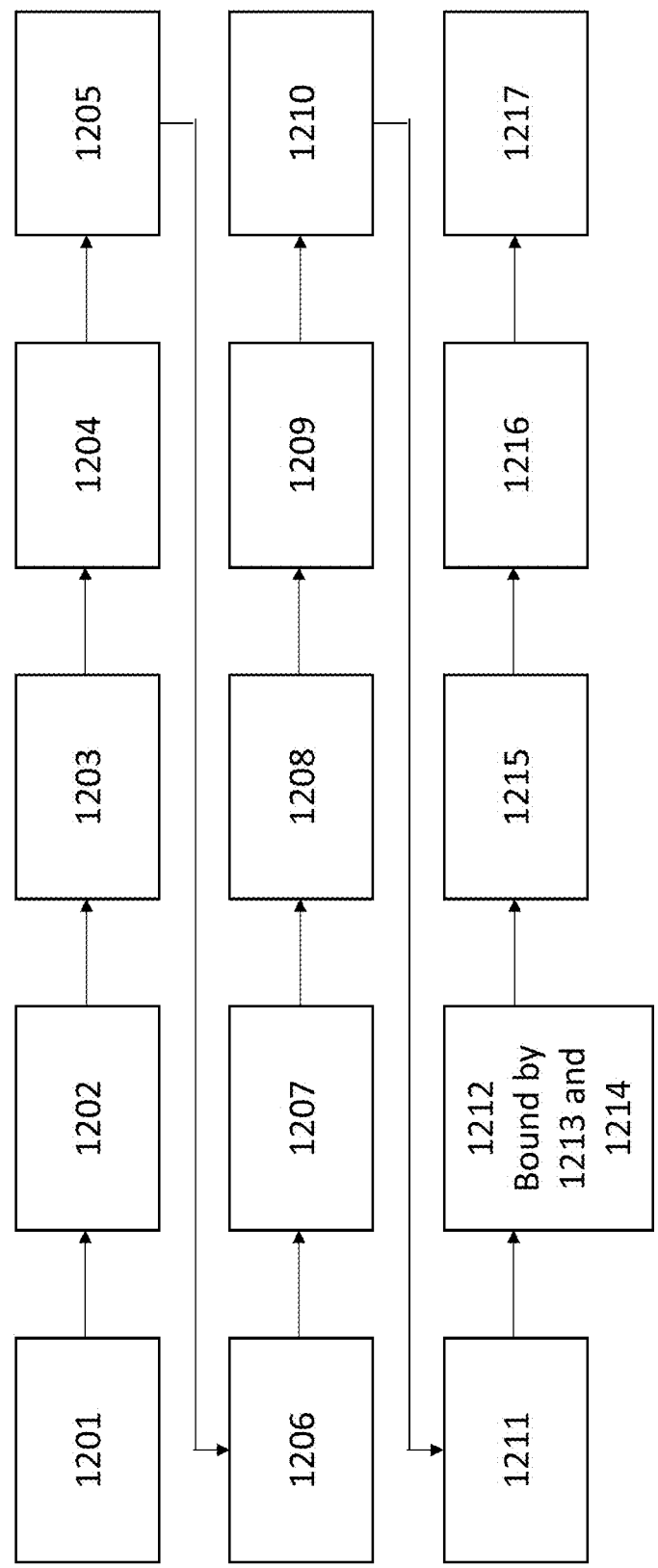
FIG. 12 shows a representation of a process for another embodiment of a design optimization phase, e.g., pseudo code.

FIG. 12 shows a flow diagram for a representing the process for the multidisciplinary design optimization phase (pseudo code). The process begins by defining the initial deep brain stimulation parameters 1201, such as parameter configuration variables (such as amplitude); deep brain stimulation electrode impedance (representative of resistance), anthropometric parameters (such as hand mass), and local gravitational acceleration. The quantified wearable inertial sensor signal data defining tremor response to the prescribed deep brain stimulation configuration parameter is uploaded 1202. The inertial signal data (accelerometer, or accelerometer and gyroscope) and post-process accelerometer signal is acquired 1203 to derive acceleration magnitude, hereafter referred to as post-processed inertial signal data. Post-processed inertial signal data is parsed 1204 into equivalent time intervals, such as two second intervals of the post-processed inertial signal data.

Post-processed inertial signal data is visualized 1205. Within each time interval the maximal acceleration and corresponding velocity is ascertained 1206 (velocity corresponding with maximal acceleration, which are derived from the post-processed inertial signal data). Step 1206 is continued 1207 for each post-processed inertial signal data time interval. Tremor power for each time interval as a function of hand mass, tremor acceleration (maximal acceleration less gravitation acceleration), and corresponding velocity is derived 1208. The mean tremor power in accordance with the total number of time interval sequences for the respective post-processed inertial signal data is derived 1209. DBS power as a function of one of the parameter configuration settings (e.g., amplitude (input current)) for deep brain stimulation and deep brain stimulation electrode impedance (resistance) is derived 1210. Effective power as a function of the square root of tremor power multiplied by square root of DBS Power is derived 1211. Steps 1201 through 1211 are repeated 1212 for the series of equally incremented deep brain stimulation parameter configuration settings (e.g., amplitude) between prescribed upper bound 1213 and lower bound 1214 settings with other parameter configuration settings held constant. Normalized effective power based on the effective power with the greatest magnitude is derived 1215. The normalized effective power as a function of the parameter configuration setting being measured (e.g., amplitude (input current)) for deep brain stimulation is visualized 1216. The parameter configuration setting (e.g., amplitude (input current)) for deep brain stimulation corresponding with the minimal normalized effective power is selected 1217. The selected parameter configuration setting (e.g., amplitude (input current)) for deep brain stimulation with the other parameter configuration settings held constant constitutes the optimal parameter configuration for deep brain stimulation.

The process demonstrated in FIG. 12 pertains to the optimization deep brain stimulation of a single parameter, such as amplitude, with respect to a parameter configuration. Other single parameters, such as stimulation frequency, pulse width, and polarity, within the parameter configuration can be prioritized instead of amplitude at the discretion of those conducting the optimization endeavor.

Figure 13A:
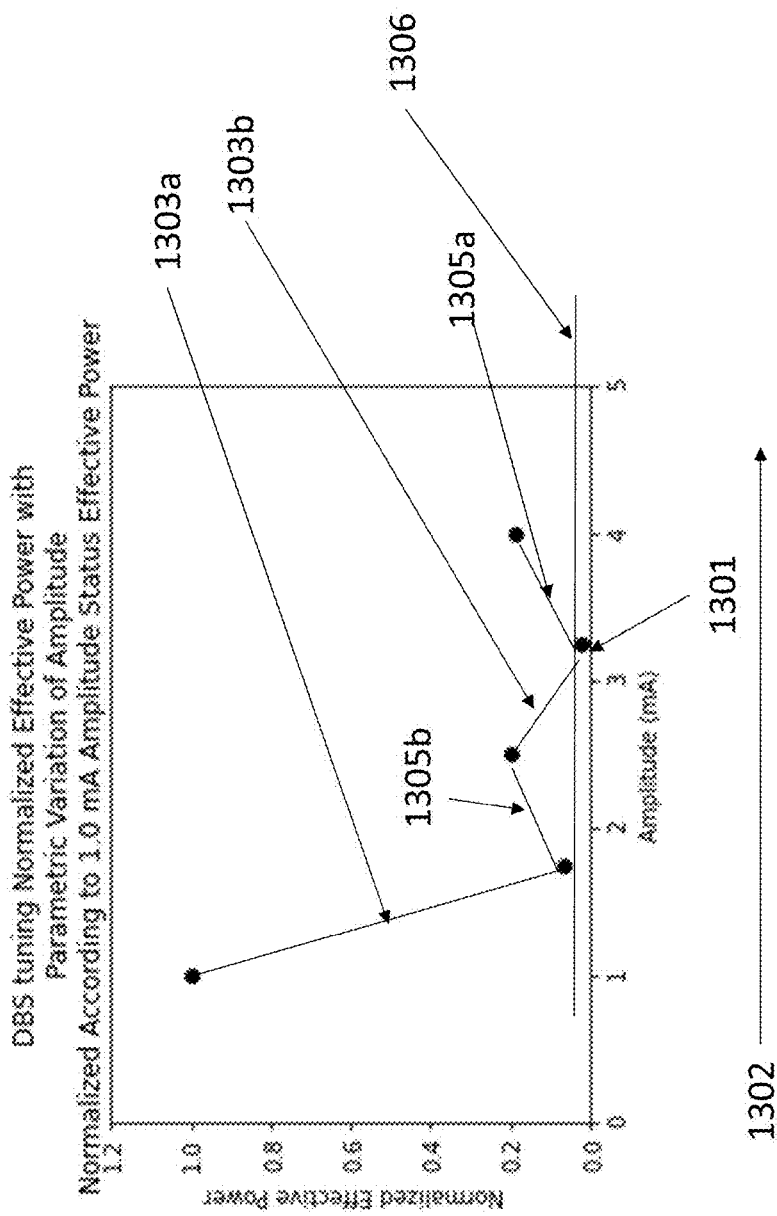
FIGS. 13a-13d show examples of modifications to general pseudo code (reducing series of amplitude increments).

FIGS. 13*a*-13*d* show modifications to the general pseudo code (reducing series of amplitude increments) as described in the example in FIG. 10. FIG. 13*a* shows an embodiment of achieving and optimal effective power 1301 that can be derived from proceeding from low to high amplitude 1302 with the optimal effective power 1301 being ascertained from descending slope of effective power 1303*a*, 1303*b* per amplitude then proceeding to ascending slope of effective power 1305*a*, 1305*b* per amplitude while the optimal effective power 1301 proceeds below a sufficient threshold 1306. The threshold can be prescribed by those conducting the optimization endeavor, such as a supervising clinical team.

Figure 13B:
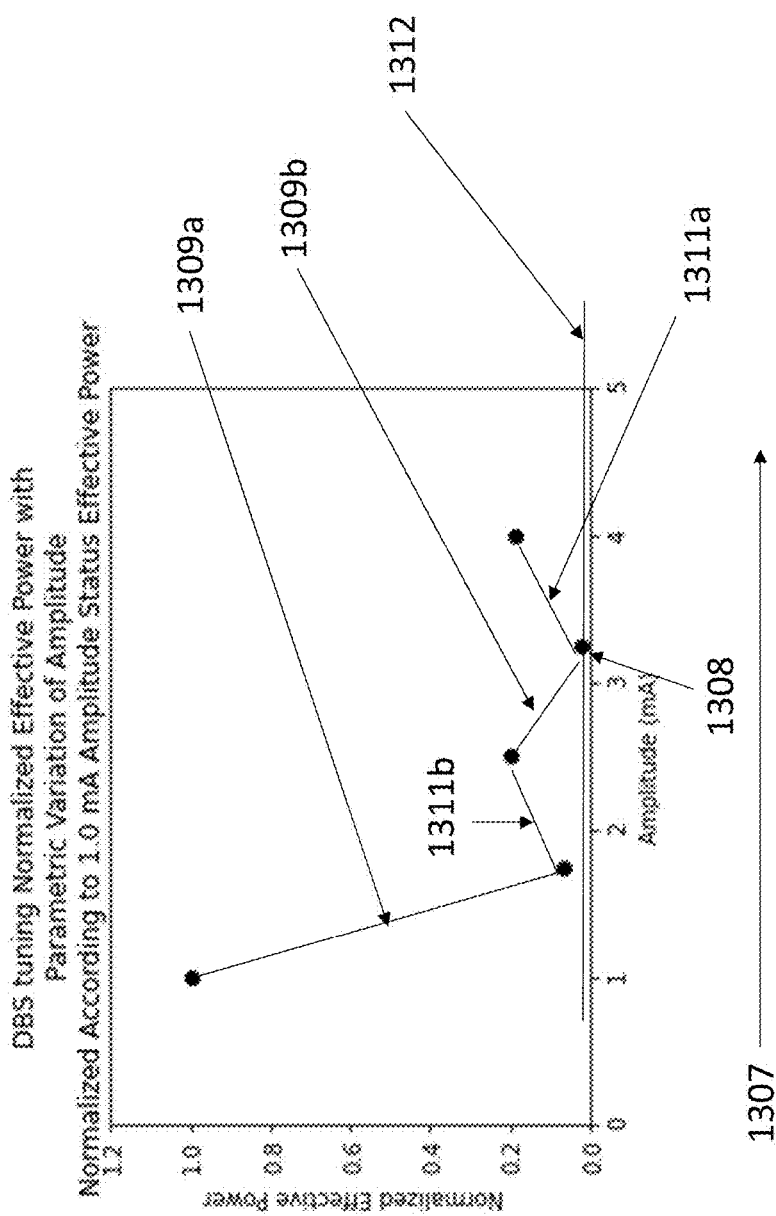

FIG. 13*b* shows another scenario from low to high amplitude 1307 involving selecting the minimal optimal effective power 1308 from descending slope of effective power 1309*a*, 1309*b* per amplitude then proceeding to ascending slope of effective power 1311*a*, 1311*b* per amplitude, although in this example the minimal optimal effective power 1308 does not proceed below a sufficient threshold 1312. This scenario constitutes a plausible optimization scenario, for which a less than desired minimal optimal effective power is ascertained.

Figure 13C:
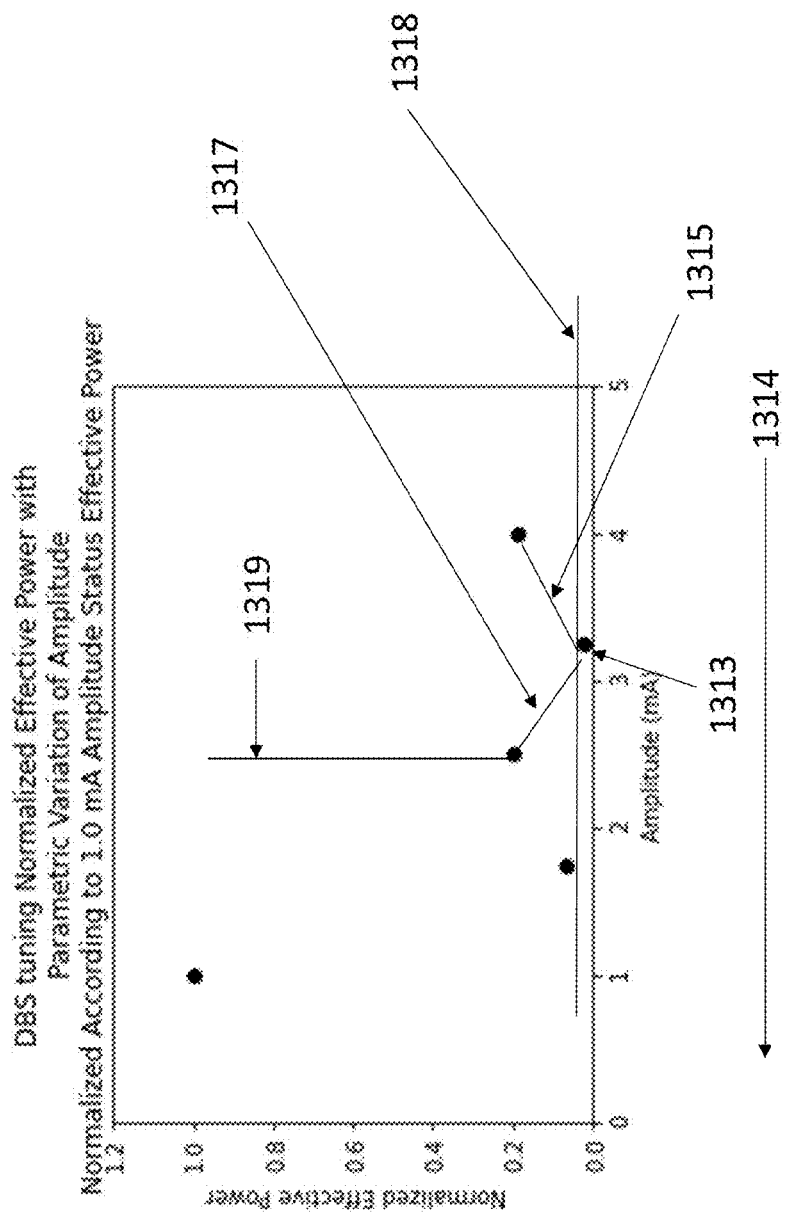

FIG. 13*c* shows another embodiment of achieving and optimal effective power 1313 that can be derived from proceeding from high to low amplitude 1314 with the optimal effective power 1313 being ascertained by the ascending slope of effective power 1315 per amplitude then proceeding to descending slope of effective power 1317 per amplitude while the optimal effective power 1313 proceeds below a sufficient threshold 1318, for which the incrementing of the amplitude terminates 1319. This scenario constitutes a plausible optimization scenario, for which a prescribed threshold eliciting a terminating amplitude enables more computationally efficient means of ascertaining the optimal effective power. This strategy can benefit situations that are inherently constrained due to limited computational resources.

Figure 13D:
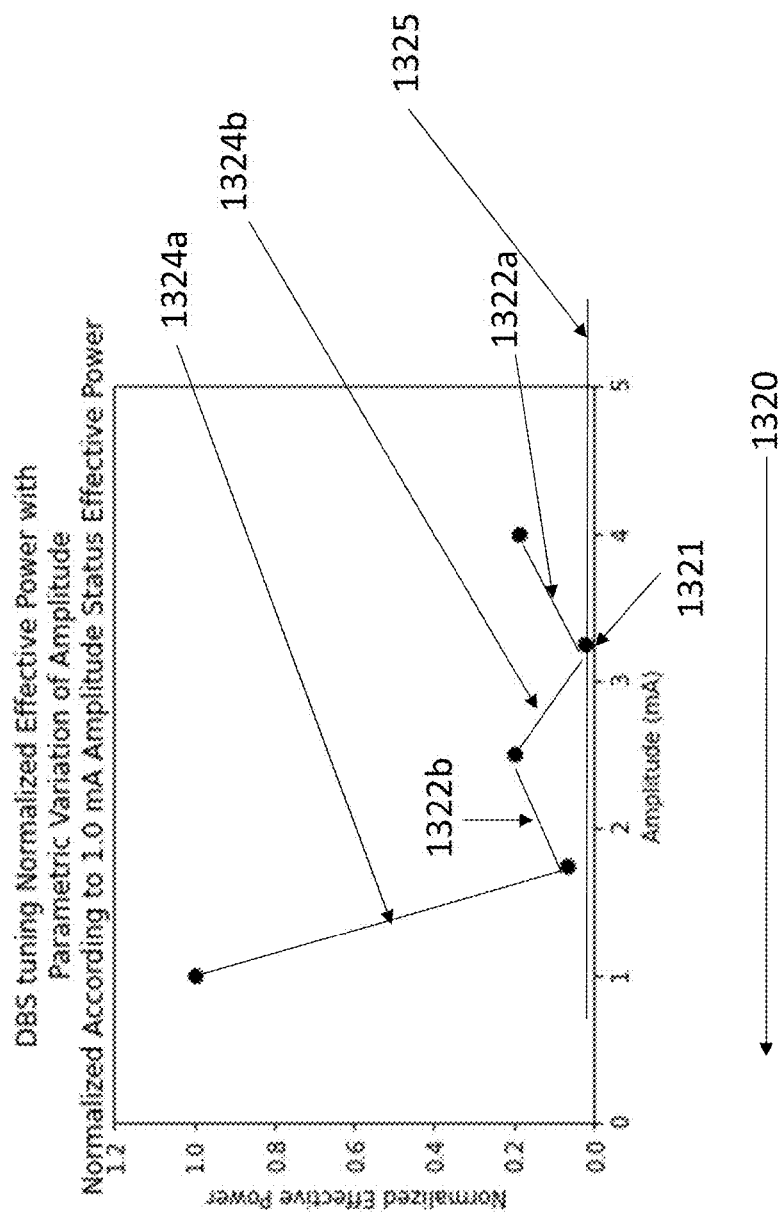

FIG. 13*d* shows another scenario from high to low amplitude 1320 involving selecting the minimal optimal effective power 1321 from the ascending slope of effective power 1322*a*, 1322*b* per amplitude then proceeding to descending slope of effective power 1324*a*, 1324*b* per amplitude although the minimal optimal effective power 1321 does not proceed below a sufficient threshold 1325. This scenario constitutes a plausible optimization scenario, for which a less than desired minimal optimal effective power is ascertained. The high to low amplitude strategy offers an alternative means to evaluate the deep brain stimulation effective power with variation of amplitude.

Other embodiments of the above process elucidated in FIGS. 13*a*-13*d* could utilize alternative parameters within the available parameter configuration for deep brain stimulation, such as stimulation frequency, pulse width, and polarity.

Figure 14:
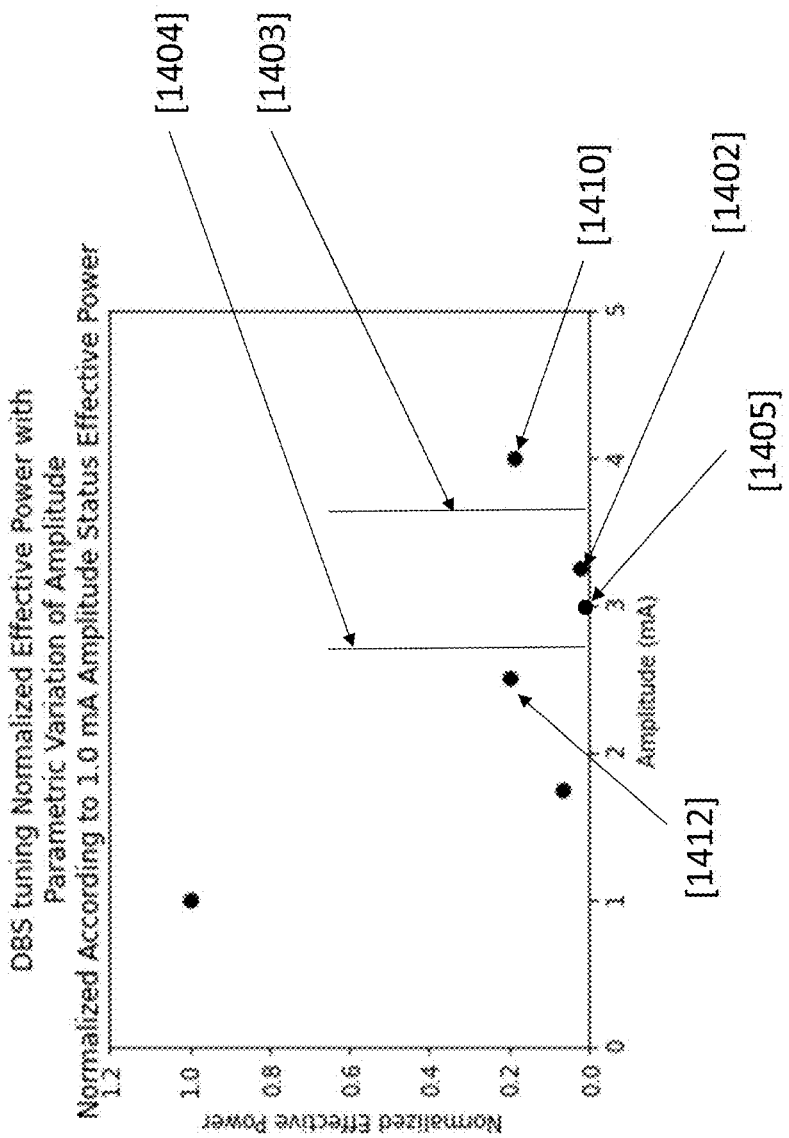
FIG. 14 shows another example of a modification to general pseudo code (reducing series of amplitude increments).

FIG. 14 shows a modification to general pseudo code (reducing series of amplitude increments) as described in FIG. 10. Once the normalized effective power as a function of amplitude visualizes the global optimal for effective power 1402, further investigation of the region about the global optimal for effective power 1402 can be elucidated. Prescribed upper bound 1403 and lower bound 1404 can be refined to localize a better global optimal for effective power 1405. For example, once a first global optimal for effective power 1402 is identified, the process can be repeated using a new upper bound 1403 that is greater than the current global optimal for effective power 1402, but less than the next highest point measured 1410; and a new lower bound 1404 that is less than the current global optimal for effective power 1402, but greater than the immediately preceding point 1412 to the current global optimal for effective power 1402. For a single parameter of the parameter configuration (in this example, it is amplitude) the process prescribed in FIG. 12 may be applied. For multiple parameters of the parameter configuration, the process prescribed in FIG. 15 may be applied. The processes in FIGS. 12 and 15 can be independently applied without the application of FIG. 14.

Figure 15:
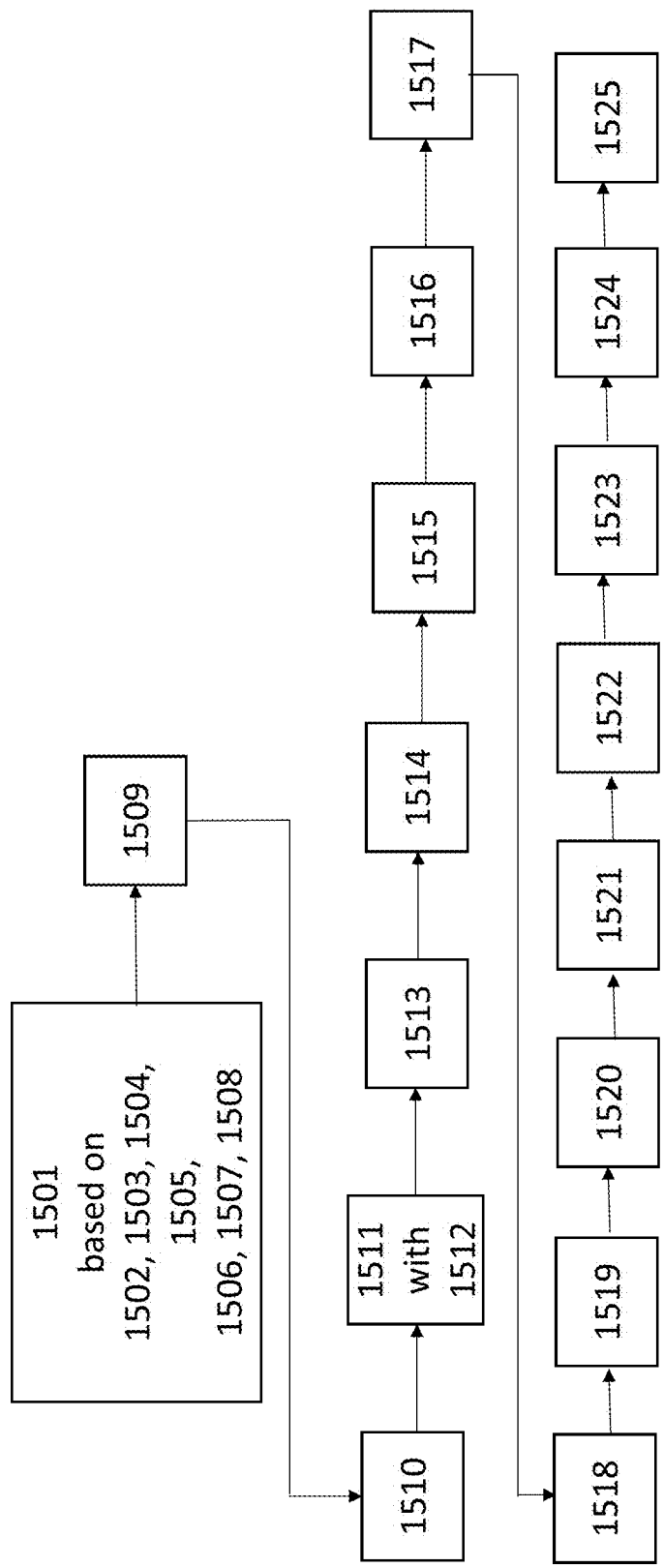
FIG. 15 shows another example of a modification to general pseudo code; multiple, such as four, independent variables by achieving optimal independent variables in ascending order of clinically prescribed priority.

FIG. 15 shows a modification to the general pseudo code with multiple (such as four) independent variables by achieving optimal independent variables in ascending order of clinically prescribed priority. In this example, a prescribe order 1501 of optimal prescribed parameter configuration variables 1502 is established in sequential order as follows: first, amplitude 1503; second, stimulation frequency 1504; third, pulse width 1505; and fourth, polarity 1506 with prescribed upper bound 1507 and lower bound 1508. The pseudo code is applied sequentially 1509 to the selected parameter configuration settings. For example, the pseudo code can be applied first to amplitude 1503, then to stimulation frequency 1504, next to pulse width 1505, and finally to polarity 1506. Other sequential orders may be prescribed at the discretion of those conducting the optimization endeavor.

Applying the pseudo code comprises, defining the initial deep brain stimulation parameter settings 1510, such as the parameter configuration variables (such as amplitude); deep brain stimulation electrode impedance (representative of resistance), anthropometric parameters (such as hand mass), and local gravitational acceleration; upload quantified wearable inertial sensor signal data 1511, which define tremor response to prescribed deep brain stimulation configuration parameter, inclusive of optimal prescribed parameter configuration variable 1512; acquire inertial signal data (accelerometer or accelerometer and gyroscope) and post-process accelerometer signal 1513 to derive acceleration magnitude, hereafter referred to as post-processed inertial signal data; parse post-processed inertial signal data into equivalent time intervals 1514, such as two second intervals of the post-processed inertial signal data; visualize post-processed inertial signal data 1515; within each time interval ascertain the maximal acceleration and corresponding velocity 1516 (velocity corresponding with maximal acceleration), which are derived from the post-processed inertial signal data; continue step 1516 for each post-processed inertial signal data time interval 1517; derive tremor power for each time interval 1518 as a function of hand mass, tremor acceleration (maximal acceleration less gravitation acceleration), and corresponding velocity; derive mean tremor power 1519 in accordance with the total number of time interval sequences for the respective post-processed inertial signal data; derive DBS power 1520 as a function of optimal prescribed parameter configuration variable 1501 for deep brain stimulation; and derive effective power 1521 as a function of the square root of tremor power multiplied by square root of DBS Power. Steps 1510 through 1521 can be repeated 1522 for the series of equally incremented deep brain stimulation optimal prescribed parameter configuration variable 1502 between prescribed upper bound 1507 and lower bound 1508 settings with other parameter configuration settings held constant. The process continues by deriving normalized effective power 1523 based on the effective power with the greatest magnitude; visualizing the normalized effective power 1524 as a function optimal prescribed parameter configuration variable 1501 for deep brain stimulation; and then selecting the optimal prescribed parameter configuration variable for deep brain stimulation corresponding with the minimal normalized effective power 1525. The selected optimal prescribed parameter configuration variable 1502 for deep brain stimulation with the other parameter configuration settings held constant constitutes the optimal parameter configuration for deep brain stimulation.

Figure 16:
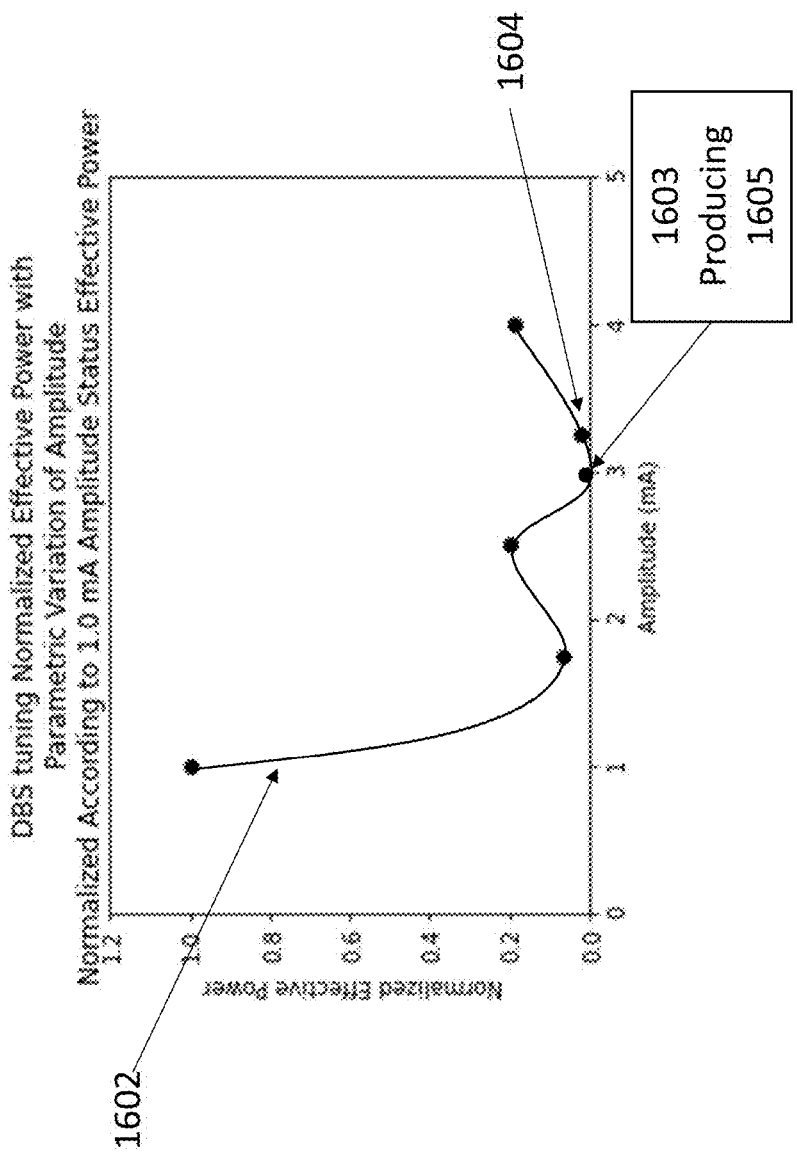
FIG. 16 shows a regression to achieve optimal (interpolation spline).

FIG. 16 shows a regression to achieve an even better optimal (interpolation spline) based on the set up as described in FIG. 10. The acquired normalized effective power as a function of one of the parameter configuration settings (e.g. amplitude) can have a regression algorithm 1602 applied. The regression algorithm 1602 can ascertain a better global optimal amplitude 1603 relative to the original global optimal amplitude 1604, which produces a more optimal parameter configuration 1605 that is ascertained by the regression algorithm 1602, such as an interpolation spline, through the context of interpolation.

The system can take the form of an entirely hardware embodiment, an entirely software embodiment or an embodiment containing both hardware and software elements. In one embodiment, the system is implemented in software, which includes but is not limited to firmware, resident software, microcode, etc.

Furthermore, the system can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium comprise a semiconductor or solid-state memory, magnetic tape, a removable computer diskette, a random access memory (RAM), a read-only memory (ROM), a rigid magnetic disk and an optical disk. Current examples of optical disks comprise compact disk-read only memory (CD-ROM), compact disk-read/write (CD-R/W) and DVD.

A data processing system suitable for storing and/or executing program code comprises at least one processor coupled directly or indirectly to memory elements through a system bus. The memory elements can include local memory employed during actual execution of the program code, bulk storage, and cache memories that provide temporary storage of at least some program code in order to reduce the number of times code is retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Described above, aspects of the present application can be embodied in a World Wide Web ("WWW") or ("Web") site accessible via the Internet. As is well known to those skilled in the art, the term "Internet" refers to the collection of networks and routers that use the Transmission Control Protocol/Internet Protocol ("TCP/IP") to communicate with one another. The internet can include a plurality of local area networks ("LANs") and a wide area network ("WAN") that are interconnected by routers. The routers are special purpose computers used to interface one LAN or WAN to another.

Furthermore, computers and other related electronic devices can be remotely connected to either the LANs or the WAN via a digital communications device, modem and temporary telephone, or a wireless link. It will be appreciated that the internet comprises a vast number of such interconnected networks, computers, and routers.

As is appreciated by those skilled in the art, the WWW is a vast collection of interconnected or "hypertext" documents written in HTML, or other markup languages, that are electronically stored at or dynamically generated by "WWW sites" or "Web sites" throughout the Internet. Additionally, client-side software programs that communicate over the Web using, for example, the TCP/IP protocol are part of the WWW. Other interactive hypertext environments may include proprietary environments such as those provided by online service providers, as well as the "wireless Web" provided by various wireless networking providers, especially those in the cellular phone industry. It will be appreciated that the present application could apply in any such interactive communication environments, however, for purposes of discussion, the Web is used as an exemplary interactive hypertext environment with regard to the present application.

A website is a server/computer connected to the Internet that has massive storage capabilities for storing hypertext documents and that runs administrative software for handling requests for those stored hypertext documents as well as dynamically generating hypertext documents. Embedded within a hypertext document can be a number of hyperlinks, i.e., highlighted portions of text which link the document to another hypertext document possibly stored at a website elsewhere on the Internet. Each hyperlink can be assigned a URL that provides the name of the linked document on a server connected to the Internet. Known to those skilled in the art, a web server may also include facilities for storing and transmitting application programs. Likewise, a web server may also include facilities for executing scripts and other application programs on the web server itself.

A remote access user may retrieve information, such as hypertext documents and other data, from the World Wide Web via a web browser program. Upon request from the remote access user via the web browser, the web browser requests the desired information from the appropriate web server using the URL for the document. The WWW browser may also retrieve programs from the web server for execution on the client computer. Finally, the WWW browser may include optional software components, called plug-ins, that run specialized functionality within the browser.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

What is claimed is:

1. A system for deep brain stimulation ("DBS") for achieving an optimal deep brain stimulation parameter configuration for treating a movement disorder, the system comprising:
   a) a wearable inertial sensor system with wireless access to a cloud computing resource, the wearable inertial sensor system configured to provide quantified feedback of a response to neuromodulation intervention that contributes to a computation of a multidisciplinary design optimization dependent variable; and
   b) a computer system equipped with a machine learning algorithm to diagnose a need to activate a multidisciplinary design optimization process when a classification accuracy, defined as correctly classified instances divided by total number of instances, proceeds below a prescribed threshold,
   c) wherein the computer system equipped with a multidisciplinary design optimization algorithm is configured to apply the multidisciplinary design optimization process to achieve an optimized dependent variable based on independent variables available from a deep brain stimulation parameter configuration,
   d) wherein the computer system is configured to control an implantable pulse generator and deliver a signal based on the optimized dependent variable for deep brain stimulation.

2. The system of claim 1, wherein the optimized dependent variable is derived from a minimal effective power, wherein the minimal effective power is a function of a tremor power raised to a first exponent, multiplied by a deep brain stimulation power raised to a second exponent, wherein a sum of the first and second exponents is 1.

3. The system of claim 2, wherein the multidisciplinary optimization process is achieved through the multidisciplinary design optimization algorithm selected from the group consisting of a gradient based algorithm, a gradient-free algorithm, and a population-based algorithm.

4. The system of claim 3, wherein the wearable inertial sensor system comprises an inertial sensor to measure and record inertial signal data to derive the tremor power.

5. The system of claim 3, wherein the deep brain stimulation power is derived from a computation of the independent variables based on a status of the deep brain stimulation parameter configuration.

6. The system of claim 3, wherein the computer system is configured for manually varying the independent variables based on a status of the parameter configurations.

7. The system of claim 3, wherein the computer system is further configured for automatically varying the independent variables based on a status of the parameter configurations incrementally in real time.

8. A method for treating a movement disorder of a patient in need thereof using deep brain stimulation to achieve an optimal deep brain stimulation parameter configuration, the method comprising:
   a) generating a quantified feedback from a wearable inertial sensor system with wireless access to a cloud computing resource system that contributes to a computation of a multidisciplinary design optimization dependent variable;
   b) executing a computer system equipped with a machine learning algorithm to diagnose a need to activate a multidisciplinary design optimization process when a classification accuracy, defined as correctly classified instances divided by total number of instances, proceeds below a prescribed threshold;
   c) executing the computer system equipped with a multidisciplinary design optimization algorithm to achieve an optimized dependent variable based on independent variables available from a deep brain stimulation parameter configuration; and
   d) stimulating a nervous system of the patient based on the optimized dependent variable to reduce tremor, wherein the movement disorder is treated.

9. The method of claim 8, further comprising deriving the optimized dependent variable from a minimal effective power, wherein the minimal effective power is a function of a tremor power raised to a first exponent, multiplied by a deep brain stimulation power raised to a second exponent, wherein a sum of the first and second exponents is 1.

10. The method of claim 9, further comprising achieving the multidisciplinary optimization process through the computer system equipped with the multidisciplinary design optimization algorithm selected from the group consisting of a gradient based algorithm, a gradient-free algorithm, and a population-based algorithm.

11. The method of claim 10, further comprising measuring and recording inertial signal data to derive the tremor power from an inertial sensor on the wearable inertial sensor system.

12. The method of claim 10, further comprising deriving the deep brain stimulation power computed by the independent variables based on a status of the deep brain stimulation parameter configuration.

13. The method of claim 10, further comprising the computer system manually varying the independent variables based on a status of the deep brain stimulation parameter configuration.

14. The method of claim 10, further comprising the computer system automatically varying the independent variables based on a status of the deep brain stimulation parameter configuration incrementally in real time.

15. A neuromodulation system for achieving an optimal neuromodulation input parameter configuration, the neuromodulation system comprising:
- a) a wearable inertial sensor system configured to provide quantified feedback of a response to neuromodulation intervention that contributes to a computation of a multidisciplinary design optimization dependent variable; and
- b) a computer system equipped with a machine learning algorithm to diagnose a need to activate a multidisciplinary design optimization process when a classification accuracy proceeds below a prescribed threshold,
- c) wherein the computer system equipped with a multidisciplinary design optimization algorithm is configured to apply a multidisciplinary design optimization process to achieve an optimized dependent variable based on independent variables available from a neuromodulation parameter configuration,
- d) wherein the neuromodulation system is configured to control an implantable pulse generator and deliver a signal based on the optimized dependent variable for deep brain stimulation.

16. The neuromodulation system of claim 15, wherein the optimized dependent variable is derived from a minimal dependent variable as a function of established performance parameters raised to a first exponent, and established cost parameters raised to a second exponent, wherein a sum of the first and second exponents is 1.

17. The neuromodulation system of claim 16, wherein the optimization process is achieved through the multidisciplinary design optimization algorithm.

18. The neuromodulation system of claim 17, wherein the wearable inertial sensor system comprises a sensor to measure and record established performance parameters.

19. The neuromodulation system of claim 17, wherein the established cost parameters are derived from the independent variables based on independent parameters available from the neuromodulation system parameter configuration.

20. The neuromodulation system of claim 17, wherein the computer system is configured to vary independent variables based on a status of the neuromodulation parameter configuration that is modified according to multidisciplinary design optimization in a manner that can be incremented in real time increments to achieve the effect of automation.

* * * * *